United States Patent
Hare, II et al.

(10) Patent No.: US 11,301,996 B2
(45) Date of Patent: Apr. 12, 2022

(54) TRAINING NEURAL NETWORKS OF AN AUTOMATIC CLINICAL WORKFLOW THAT RECOGNIZES AND ANALYZES 2D AND DOPPLER MODALITY ECHOCARDIOGRAM IMAGES

(71) Applicant: EKO.AI PTE. LTD., Singapore (SG)

(72) Inventors: James Otis Hare, II, Singapore (SG);
Paul James Seekings, Singapore (SG);
Su Ping Carolyn Lam, Singapore (SG); Yoran Hummel, Singapore (SG);
Jasper Tromp, Singapore (SG);
Wouter Ouwerkerk, Singapore (SG);
Zhubo Jiang, Singapore (SG)

(73) Assignee: EKO.AI PTE. LTD., Singapore (SG)

( * ) Notice: Subject to any disclaimer, the term of this patent is extended or adjusted under 35 U.S.C. 154(b) by 112 days.

(21) Appl. No.: 16/833,001

(22) Filed: Mar. 27, 2020

(65) Prior Publication Data
US 2020/0226757 A1    Jul. 16, 2020

Related U.S. Application Data

(63) Continuation-in-part of application No. 16/216,929, filed on Dec. 11, 2018, now Pat. No. 10,631,828.

(51) Int. Cl.
*G06T 7/00*   (2017.01)
*G16H 40/67*  (2018.01)
(Continued)

(52) U.S. Cl.
CPC .......... *G06T 7/0012* (2013.01); *G06N 3/0454* (2013.01); *G06N 3/08* (2013.01);
(Continued)

(58) Field of Classification Search
CPC ....... A61B 8/5223; A61B 8/5207; A61B 8/06; A61B 8/488; A61B 8/54; A61B 8/14;
(Continued)

(56) References Cited

U.S. PATENT DOCUMENTS 7,087,018 B2    8/2006  Comaniciu
7,421,101 B2    9/2008  Georgescu
(Continued)

FOREIGN PATENT DOCUMENTS

WO   2017/009812 A1    1/2017
WO   2017/181288 A1    10/2017
(Continued)

OTHER PUBLICATIONS

Patent Cooperation Treaty: International Search Report and Written Opinion for PCT/IB2018/001591 dated Sep. 9, 2019; 7 pages.
(Continued)

*Primary Examiner* — Bobbak Safaipour
(74) *Attorney, Agent, or Firm* — Schwabe, Williamson & Wyatt, PC

(57) ABSTRACT

A method for training neural networks of an automated workflow performed by a software component executing on a server in communication with remote computers at respective laboratories includes downloading and installing a client and a set of neural networks to a first remote computer of a first laboratory, the client accessing the echocardiogram image files of the first laboratory to train the set of neural networks and to upload a first trained set of neural networks to the server. The process continues until the client and the second trained set of neural networks is downloaded and installed to a last remote computer of a last laboratory, the client accessing the echocardiogram image files of the last
(Continued)

laboratory to continue to train the second trained set of neural networks and to upload a final trained set of neural networks to the server.

25 Claims, 21 Drawing Sheets

(51) Int. Cl.
| | |
|---|---|
| *G16H 40/63* | (2018.01) |
| *G16H 30/40* | (2018.01) |
| *G16H 30/20* | (2018.01) |
| *G06T 7/11* | (2017.01) |
| *G06N 3/08* | (2006.01) |
| *G06N 3/04* | (2006.01) |

(52) U.S. Cl.
CPC .............. *G06T 7/11* (2017.01); *G16H 30/20* (2018.01); *G16H 30/40* (2018.01); *G16H 40/63* (2018.01); *G16H 40/67* (2018.01); *G06T 2207/10132* (2013.01); *G06T 2207/20081* (2013.01); *G06T 2207/20084* (2013.01); *G06T 2207/30048* (2013.01)

(58) Field of Classification Search
CPC ...... G16H 30/20; G16H 30/40; G06T 7/0012; G06T 2207/30048; G06T 2207/10132
See application file for complete search history.

(56) References Cited

U.S. PATENT DOCUMENTS

| | | | |
|---|---|---|---|
| 7,458,936 B2 | 12/2008 | Zhou | |
| 8,092,388 B2 | 1/2012 | Park | |
| 8,396,531 B2 | 3/2013 | Zhou | |
| 8,744,152 B2 | 6/2014 | Beymer | |
| 8,917,917 B2 | 12/2014 | Beymer | |
| 9,280,819 B2 | 3/2016 | Codella | |
| 9,842,390 B2 | 12/2017 | Syeda-Mahmood | |
| 9,918,023 B2 | 3/2018 | Simolon et al. | |
| 9,924,116 B2 | 3/2018 | Chahine et al. | |
| 9,930,324 B2 | 3/2018 | Chahine et al. | |
| 9,984,283 B2 | 5/2018 | Davatzikos | |
| 10,033,944 B2 | 7/2018 | Hogasten et al. | |
| 10,044,946 B2 | 8/2018 | Strandemar et al. | |
| 10,091,439 B2 | 10/2018 | Hogasten et al. | |
| 10,122,944 B2 | 11/2018 | Nussmeier et al. | |
| 10,143,390 B2* | 12/2018 | Ledoux ................ A61B 5/7225 |
| 10,182,195 B2 | 1/2019 | Kostrzewa et al. | |
| 10,192,540 B2 | 1/2019 | Clarke et al. | |
| 10,230,909 B2 | 3/2019 | Kostrzewa et al. | |
| 10,230,910 B2 | 3/2019 | Boulanger et al. | |
| 10,244,190 B2 | 3/2019 | Boulanger et al. | |
| 10,249,032 B2 | 4/2019 | Strandemar | |
| 10,250,822 B2 | 4/2019 | Terre et al. | |
| 10,338,800 B2 | 7/2019 | Rivers et al. | |
| 10,425,603 B2 | 9/2019 | Kostrzewa et al. | |
| 10,436,887 B2 | 10/2019 | Stokes et al. | |
| 10,598,550 B2 | 3/2020 | Christel et al. | |
| 10,623,667 B2 | 4/2020 | Hogasten et al. | |
| 10,631,828 B1 | 4/2020 | Hare | |
| 10,702,247 B2 | 7/2020 | Hare, II | |
| 10,803,553 B2 | 10/2020 | Foi et al. | |
| 10,909,660 B2 | 2/2021 | Egiazarian et al. | |
| 10,937,140 B2 | 3/2021 | Janssens et al. | |
| 10,962,420 B2 | 3/2021 | Simolon | |
| 10,983,206 B2 | 4/2021 | Hawker | |
| 10,986,288 B2 | 4/2021 | Kostrzewa et al. | |
| 10,986,338 B2 | 4/2021 | De Muynck | |
| 10,996,542 B2 | 5/2021 | Kostrzewa et al. | |
| 11,010,878 B2 | 5/2021 | Hogasten et al. | |
| 11,012,648 B2 | 5/2021 | Kostrzewa et al. | |
| 11,029,211 B2 | 6/2021 | Frank et al. | |
| 2005/0074088 A1* | 4/2005 | Ichihara ............... G01N 23/046 378/58 |
| 2012/0221310 A1* | 8/2012 | Sarrafzadeh ......... A61B 5/7275 703/11 |
| 2013/0238363 A1* | 9/2013 | Ohta ..................... G16H 50/20 705/3 |
| 2014/0233818 A1 | 8/2014 | Thiruvenkadam | |
| 2015/0141826 A1 | 5/2015 | Beymer | |
| 2016/0203288 A1 | 7/2016 | Meng | |
| 2017/0367604 A1 | 12/2017 | Spangler | |
| 2018/0103931 A1* | 4/2018 | Negahdar ............ A61B 8/5223 |
| 2018/0107787 A1* | 4/2018 | Compas ................... G06K 9/00 |
| 2018/0107801 A1* | 4/2018 | Guo ........................ G16H 15/00 |
| 2018/0108125 A1* | 4/2018 | Beymer ................ A61B 8/5223 |
| 2018/0204364 A1 | 7/2018 | Hoffman | |
| 2018/0205893 A1 | 7/2018 | Simolon et al. | |
| 2018/0266886 A1 | 9/2018 | Frank et al. | |
| 2018/0283953 A1 | 10/2018 | Frank et al. | |
| 2018/0330474 A1 | 11/2018 | Mehta et al. | |
| 2019/0141261 A1 | 5/2019 | Hogasten et al. | |
| 2019/0228513 A1 | 7/2019 | Strandemar | |
| 2019/0325566 A1 | 10/2019 | Hogasten | |
| 2019/0335118 A1 | 10/2019 | Simolon et al. | |
| 2019/0342480 A1 | 11/2019 | Kostrzewa et al. | |
| 2019/0359300 A1 | 11/2019 | Johnson et al. | |
| 2020/0005440 A1 | 1/2020 | Sanchez-Monge et al. | |
| 2020/0090308 A1 | 3/2020 | Lin et al. | |
| 2020/0107818 A1* | 4/2020 | Keshet ................. A61B 8/5246 |
| 2020/0141807 A1 | 5/2020 | Poirier et al. | |
| 2020/0178940 A1 | 6/2020 | Hare | |
| 2020/0185084 A1* | 6/2020 | Syeda-Mahmood ....................... A61B 8/5223 |
| 2020/0193652 A1 | 6/2020 | Hoffman et al. | |
| 2020/0327646 A1 | 10/2020 | Xu et al. | |
| 2020/0397313 A1* | 12/2020 | Attia ...................... A61B 5/366 |
| 2020/0401143 A1 | 12/2020 | Johnson et al. | |
| 2021/0052252 A1* | 2/2021 | Hare, II ................. G16H 70/20 |
| 2021/0080260 A1 | 3/2021 | Tremblay et al. | |
| 2021/0219922 A1* | 7/2021 | Sevenster .............. A61B 5/339 |
| 2021/0259664 A1* | 8/2021 | Hare, II ................ A61B 8/466 |
| 2021/0264238 A1* | 8/2021 | Hare, II ................ A61B 8/14 |

FOREIGN PATENT DOCUMENTS

| | | |
|---|---|---|
| WO | 2017/205836 A1 | 11/2017 |
| WO | 2020/121014 A1 | 6/2020 |

OTHER PUBLICATIONS

Zhang et al., "A Computer Vision Pipeline for Automated Determination of Cardiac Structure and Function and Detection of Disease by Two-Dimensional Echocardiography" dated Jan. 12, 2018; 32 pages; retrieved from the Internet at <https://www.arxiv-vanity.com/papers/1706/07342/>.

* cited by examiner

PLAX - PARASTERNAL LONG AXIS

A2C - APICAL 2 CHAMBER

A3C - APICAL THREE CHAMBER

A4C - APICAL FOUR CHAMBER

A4C +PW (MV) - A4C PLUS PULSE
WAVE OF THE MITRAL VALVE

A4C + PWTDI (SEPTAL) - A4C PLUS
PULSE WAVE TISSUE DOPPLER
ON THE SEPTAL SIDE

A4C +PWTDI (LATERAL) - A4C PLUS
PULSE WAVE TISSUE
DOPPLER ON THE LATERAL SIDE

A4C + PWTDI (Tr) - A4C PLUS PULSE WAVE
TISSUE DOPPLER
ON THE TRICUSPID SIDE

A5C +CW (AoV) - A5C PLUS CONTINUOUS
WAVE OF THE AORTIC VALVE

A4C + MMODE (TrV)

A5C + PW (LVOT)

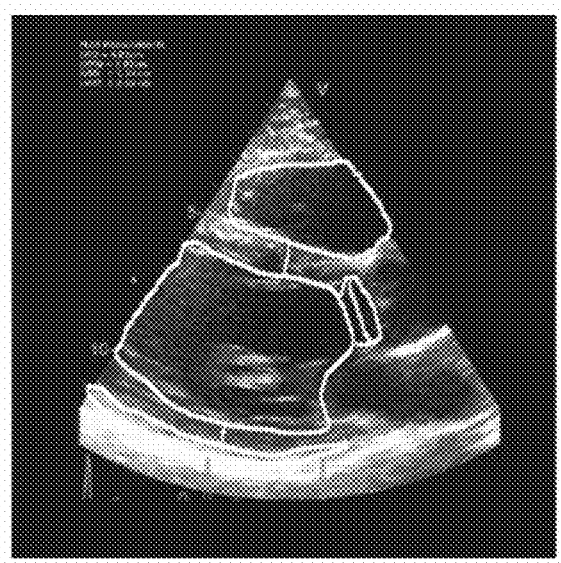 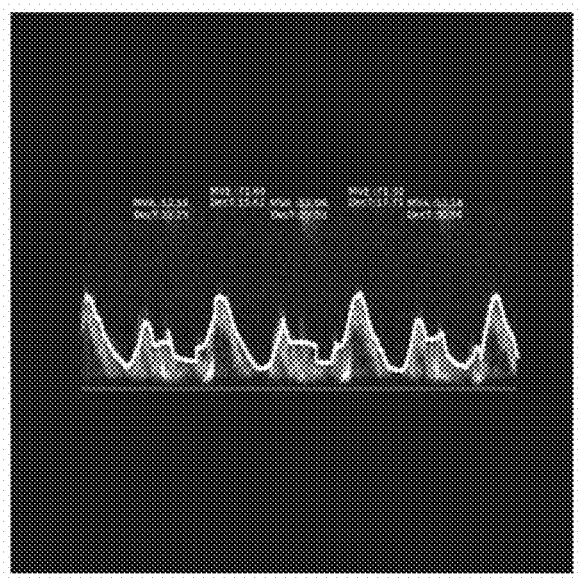
FIG. 10A  FIG. 10B
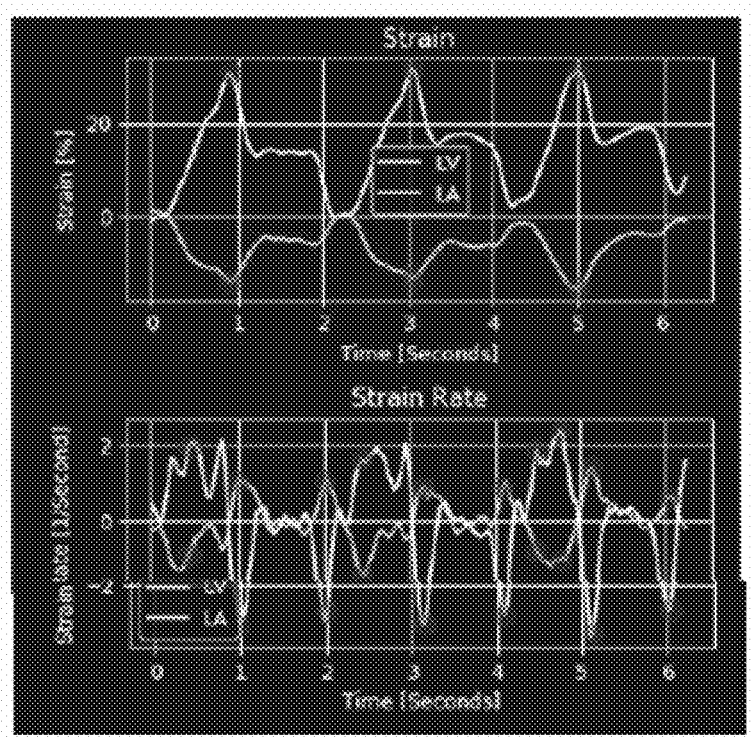
FIG. 11

1200 ↘

BEST MEAUEMENT DATA

| | | | | |
|---|---|---|---|---|
| A4C_DIASTOLE_LV_MODI | 84 | 162.1849 | 5 | 3 |
| A4C_DIASTOLE_LV_AREA | 81 | 178.2626 | 5 | 3 |
| A4C_DIASTOLE_LV_LONG | 88 | 9.742721 | 5 | 3 |
| A4C_SYSTOLE_LV_MOD | 86 | 95.7245 | 5 | 3 |
| A4C_SYSTOLE_LV_MODI | 87 | 95.7245 | 5 | 3 |
| A4C_SYSTOLE_LV_AREA | 82 | 111.611 | 5 | 3 |
| A2C_DIASTOLE_LV_LONG | 0 | 5.587553 | 5 | 3 |
| A4C_SYSTOLE_LA_MOD | 55 | 0 | 5 | 3 |
| A4C_SYSTOLE_LA_MODI | 56 | 0 | 5 | 3 |
| A4C_SYSTOLE_LA_AREA | 52 | 65.45089 | 5 | 3 |
| A4C_SYSTOLE_LA_LONG | 57 | 5.800979 | 5 | 3 |
| A4C_SYSTOLE_RA_MOD | 59 | 68.34016 | 5 | 3 |
| A4C_SYSTOLE_RA_AREA | 60 | 73.89123 | 5 | 3 |
| PLAX_SYSTOLE_LVID | 145 | 2.615142 | 18 | 3 |
| PLAX_DIASTOLE_LVID | 143 | 5.353238 | 18 | 3 |
| PLAX_DIASTOLE_LVPW | 149 | 0.694317 | 18 | 3 |
| PLAX_DIASTOLE_LVOT | 150 | 1.508679 | 18 | 3 |
| PLAX_DIASTOLE_IVSD | 141 | 1.127811 | 18 | 3 |
| TAPSE | 95 | 5.38047 | 24 | 3 |
| PW (LVOT)_VMAX | 135 | 0.109959 | 28 | 3 |
| PW (LVOT)_VMEAN | 136 | 14.85664 | 28 | 3 |
| PW (LVOT)_VTI | 140 | 1138.244 | 28 | 3 |
| A2C_DIASTOLE_LV_MOD | 21 | 168.3154 | 30 | 3 |
| A2C_DIASTOLE_LV_MODI | 22 | 168.3154 | 30 | 3 |
| A2C_DIASTOLE_LV_AREA | 19 | 179.9563 | 30 | 3 |
| A2C_SYSTOLE_LV_MOD | 24 | 87.88392 | 30 | 3 |
| A2C_SYSTOLE_LV_MODI | 25 | 87.88392 | 30 | 3 |
| A2C_SYSTOLE_LV_AREA | 20 | 95.27431 | 30 | 3 |
| A2C_SYSTOLE_LV_LONG | 26 | 7.654814 | 30 | 3 |
| A2C_SYSTOLE_LA_MOD | 16 | 72.50261 | 30 | 3 |
| A2C_SYSTOLE_LA_MODI | 17 | 72.50261 | 30 | 3 |
| A2C_SYSTOLE_LA_AREA | 14 | 83.36769 | 30 | 3 |
| A2C_SYSTOLE_LA_LONG | 18 | 6.08746 | 30 | 3 |
| CW[AoV]_VMAX | 130 | 0.14173 | 34 | 3 |
| CW[AoV]_VMEAN | 131 | 12.29993 | 34 | 3 |
| CW[AoV]_VTI | 132 | 946.4926 | 34 | 3 |
| A4C+PW (MV)_E_HEIGHT | 101 | 70.93907 | 35 | 3 |
| A4C+PW (MV)_E_DECT | 97 | 0.163194 | 35 | 3 |
| A4C+PW (MV)_A_HEIGHT | 99 | 53.58164 | 35 | 3 |

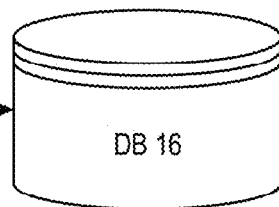

| Normal ranges for LV mass indices | | |
|---|---|---|
| | Woman | Men |
| Linear method | | |
| LV mass (g) | 67-162 | 88-224 |
| LV mass/BSA (g/m$^2$) | 43-95 | 49-115 |
| Relative wall thickness (cm) | 0.22-0.42 | 0.24-0.42 |
| Septal thickness (cm) | 0.6-0.9 | 0.6-1.0 |
| Posterior wall thickness | 0.6-0.9 | 0.6-1.0 |

FIG. 14

| ECHO WORKFLOW REPORT | |
|---|---|
| PRINT     VIEW     FLAG | |
| First name | James Hall |
| Patient ID | JH001 |
| Body surface area | |
| Referral reasons | Acute coronary |
| MAIN FINDINGS | |
| 1. LV Systolic Function | Normal |
| 2. LV Systolic Function | Normal |
| 3. Cardiac Size | Normal |
| 4. RV Function | Normal |

FIG. 15

TRAINING NEURAL NETWORKS OF AN AUTOMATIC CLINICAL WORKFLOW THAT RECOGNIZES AND ANALYZES 2D AND DOPPLER MODALITY ECHOCARDIOGRAM IMAGES

CROSS-REFERENCE TO RELATED APPLICATION

This application is a continuation-in-part of co-pending patent application Ser. No. 16/216,929, filed Dec. 11, 2018, assigned to the assignee of the present application and incorporated herein by reference.

BACKGROUND

The present invention relates to image classification for disease prediction, and more specifically, to training neural networks of an automatic clinical workflow that recognizes and analyzes 2D and doppler modality echocardiogram images for automated measurements and the diagnosis, prediction and prognosis of heart disease.

Cardiovascular disease including heart failure is a major health problem accounting for about 30% of human deaths worldwide. Heart failure is also the leading cause of hospitalization in adults over the age of 65 years. Echocardiography is an important diagnostic aid in cardiology for the morphological and functional assessment of the heart. In a typical patient echocardiogram (echo) examination, a clinician called a sonographer places an ultrasound device against the patient's chest to capture a number of 2D images/videos of the patients' heart. Reflected sound waves reveal the inner structure of the heart walls and the velocities of blood flows. The ultrasound device position is varied during an echo exam to capture different anatomical sections as 2D slices of the heart from different viewpoints or views. The clinician has the option of adding to these 2D images a waveform captured from various possible modalities including continuous wave Doppler, m-mode, pulsed wave Doppler and pulsed wave tissue Doppler. The 2D images/videos and Doppler modality images are typically saved in DICOM (Digital Imaging and Communications in Medicine) formatted files. Although the type of modality is partially indicated in the metadata of the DICOM file, the ultrasound device position in both the modality and 2D views, which is the final determinant of which cardiac structure has been imaged, is not.

After the patient examination, a clinician/technician goes through the DICOM files, manually annotates heart chambers and structures like the left ventricle (LV) and takes measurements of those structures. The process is reliant on the clinicians' training to recognize the view in each image and make the appropriate measurements. In a follow up examination, a cardiologist reviews the DICOM images and measurements, compares them to memorized guideline values and make a diagnosis based on the interpretation made from the echocardiogram.

The current workflow process for analyzing DICOM images, measuring cardiac structures in the images and determining, predicting and prognosticating heart disease is highly manual, time-consuming and error-prone. Because the workflow process is so labor intensive, more than 95% of the images available in a typical patient echocardiographic study are never annotated or quantified. The view angle or Doppler modality type by which an image was captured is typically not labelled, which means the overwhelming majority of stored DICOMs from past patient studies and clinical trials do not possess the basic structure and necessary identification of labels to allow for machine learning on this data.

There has been a recent proposal for automated cardiac image interpretation to enable low cost assessment of cardiac function by non-experts. Although the proposed automated system holds the promise of improved performance compared to the manual process, the system has several shortfalls. One shortfall is that the system only recognizes 2D images. In addition, although the proposed system may distinguish between a normal heart and a diseased heart, the proposed system is incapable of distinguishing hearts having similar-looking diseases. Consequently, the number of heart diseases identified by the proposed system is very limited and requires manual intervention to identify other types of heart diseases.

For example, heart failure has been traditionally viewed as a failure of contractile function and left ventricular ejection fraction (LVEF) has been widely used to define systolic function, assess prognosis and select patients for therapeutic interventions. However, it is recognized that heart failure can occur in the presence of normal or near-normal EF: so-called "heart failure with preserved ejection fraction (HFPEF)" which accounts for a substantial proportion of clinical cases of heart failure. Heart failure with severe dilation and/or markedly reduced EF: so-called "heart failure with reduced ejection fraction (HFREF)" is the best understood type of heart failure in terms of pathophysiology and treatment. The symptoms of heart failure may develop suddenly 'acute heart failure' leading to hospital admission, but they can also develop gradually. Timely diagnosis, categorization of heart failure subtype-HFREF or HFPEF, and improved risk stratification are critical for the management and treatment of heart failure, but the proposed system does not address this.

The proposed system is also incapable of generating a prognosis based on the identified heart disease, and would instead require a cardiologist to manually form the prognosis. The proposed system is further incapable of structuring the automated measurements and labelled views across multiple sources of data, to enable training and validation of disease prediction algorithms across multiple remote patient cohorts.

Accordingly, there is a need for an improved and fully automatic clinical workflow that recognizes and analyzes both 2D and Doppler modality echocardiographic images and a method of training the neural networks used by the automatic clinical workflow.

BRIEF SUMMARY

The exemplary embodiments provide methods and systems for training neural networks of an automated workflow performed by a software component executing on a server in communication with remote computers at respective laboratories. Aspects of exemplary embodiment include downloading and installing a client and a set of neural networks to a first remote computer of a first laboratory, the client accesses the echocardiogram image files of the first laboratory to train the set of neural networks and to upload a first trained set of neural networks to the server. The client and the first trained set of neural networks is downloaded and installed to a second remote computer of a second laboratory, the client accesses the echocardiogram image files of the second laboratory to continue to train the first trained set of neural networks and to upload a second trained set of neural networks to the server. The process continues until the client and the second trained set of neural networks is downloaded and installed to a last remote computer of a last laboratory, the client accesses the echocardiogram image files of the last laboratory to continue to train the second trained set of neural networks and to upload a final trained set of neural networks to the server. In a further embodiment, the software component executing on the server uses the final trained set of neural networks in an analysis mode to automatically recognize and analyze the echocardiogram images in the patient studies of the respective labs.

According to the method and system disclosed herein, the disclosed embodiments provides a federated training platform that accesses structured echo image databases in multiple lab locations to allow distributed neural network training and validation of disease prediction across multiple patient cohorts without either the original echo images files or the labelled echo image files stored in the structured database ever having to leave the premise of the labs.

BRIEF DESCRIPTION OF SEVERAL VIEWS OF THE DRAWINGS

FIGS. 10A and 10B are diagrams graphically illustrating structural measurements automatically generated from annotations of cardiac chambers in a 2D image, and velocity measurements automatically generated from annotations of waveforms in a Doppler modality.

FIG. 11 is a diagram graphically illustrating measurements of global longitudinal strain that were automatically generated from the annotations of cardiac chambers in 2D images.

FIG. 12A is a diagram graphically illustrating an example set of best measurement data based on largest volume cardiac chambers and the saving of the best measurement data to a repository.

FIG. 14 is a diagram illustrating a portion of an example report showing highlighting values that are outside the range of International guidelines.

FIG. 15 is a diagram illustrating a portion of an example report of Main Findings that may be printed and/or displayed by the user.

DETAILED DESCRIPTION

The exemplary embodiments relate to training neural networks of an automatic clinical workflow that recognizes and analyzes 2D and Doppler modality Echocardiographic images. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The disclosed embodiments provide method and system for training and implementing a software-based automatic clinical workflow that recognizes and analyzes both 2D and Doppler modality Echocardiographic images for automated measurements and the diagnosis, prediction and prognosis of heart disease, and which can be deployed in workstation or mobile-based ultrasound point-of-care systems.

Figure 1A:
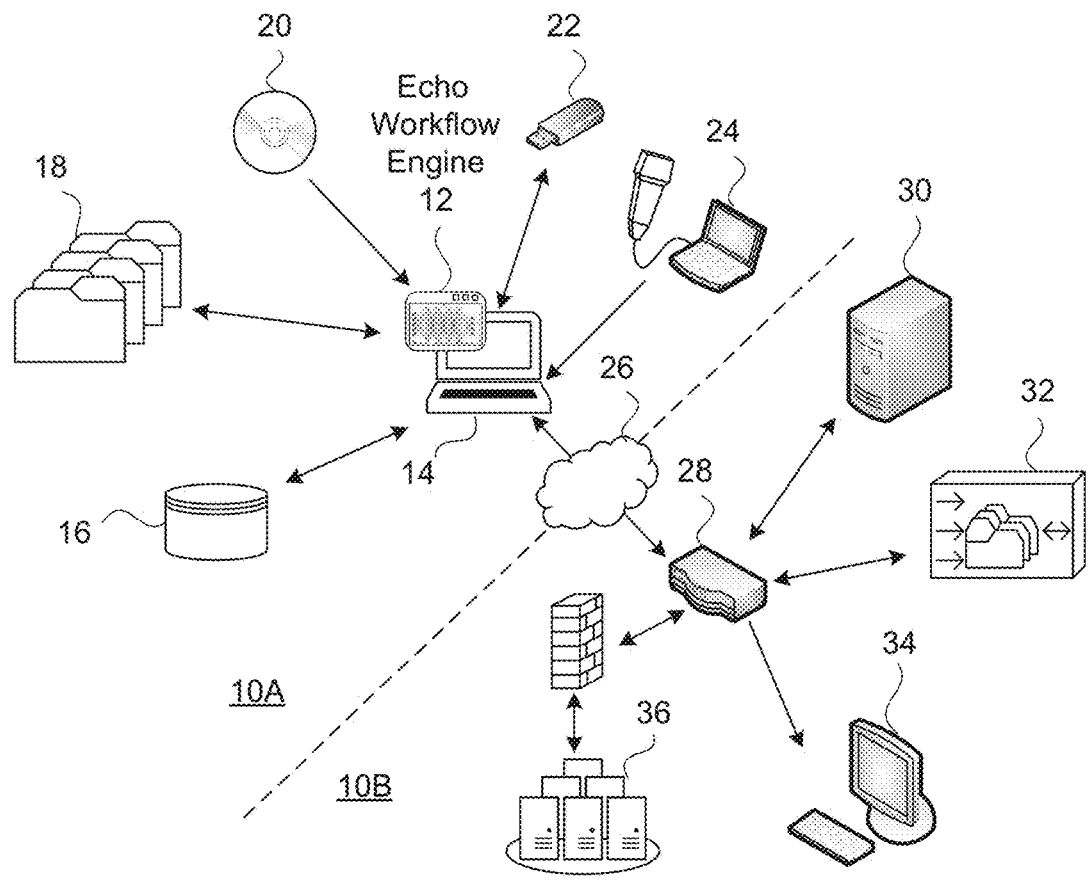
FIGS. 1A-1C are diagrams illustrating embodiments of a system for implementing an automated clinical workflow that recognizes and analyzes both 2D and Doppler modality Echocardiographic images for automated measurements and the diagnosis, prediction and prognosis of heart disease.
Figure 1B:
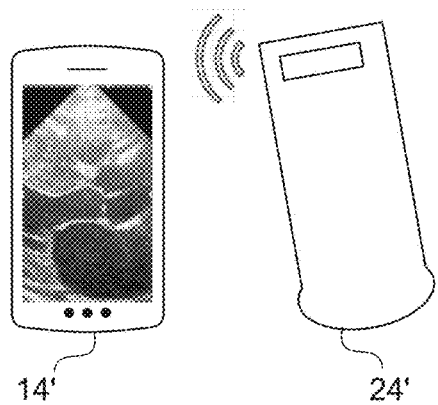
Figure 1C:
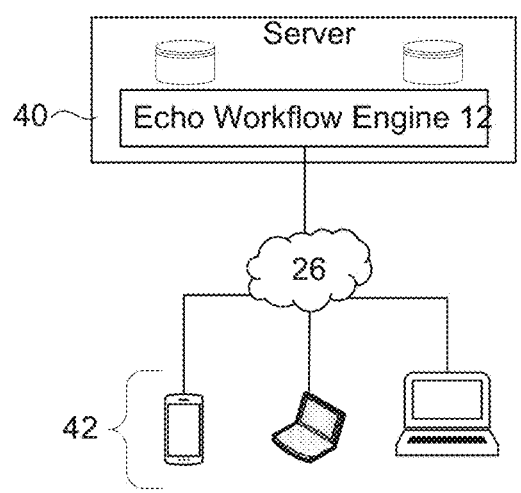

FIGS. 1A-1C are diagrams illustrating embodiments of a system for implementing an automated clinical workflow that recognizes and analyzes both 2D and Doppler modality Echocardiographic images for automated measurements and the diagnosis, prediction and prognosis of heart disease. FIG. 1A shows a basic standalone configuration for the automated clinical workflow system 10A. The automated clinical workflow 10A is primarily implemented as a software application, referred to as echo workflow engine 12, that executes on a computer 14 operating in a standalone setting, disconnected from other devices on network 26. The computer 14 may be implemented in any form factor including a workstation, desktop, notebook, laptop server or tablet capable of running an operating system, such as Microsoft Windows® (e.g., Windows 7®, Windows 10®), Apple macOS®, Linux®, Apple iOS®, Android®, and the like.

The computer 14 may include typical hardware components (not shown) including a processor, input devices (e.g., keyboard, pointing device, microphone for voice commands, buttons, touchscreen, etc.), output devices (e.g., a display device, speakers, and the like), and wired or wireless network communication interfaces (not shown) for communication. The computer 14 may include internal computer-readable media, such as memory (not shown) containing computer instructions comprising the echo workflow engine 12, which implements the functionality disclosed herein when executed by one or more computer processors.

The computer 14 may further include local internal storage for storing one or more databases 16 and an image file archive 18. In one embodiment, the contents of the image file archive 18 include echocardiogram image files (also referred to herein as echo images), which in some embodiments may be stored in DICOM (Digital Imaging and Communications in Medicine) format.

In one embodiment, the computer 14 is in communication with peripheral devices such an ultrasound imaging device 24 that captures echocardiogram images of a patient's organ (e.g., a heart), which may then be stored as a patient study using the database 16 and image file archive 18. For example, the computer 14 may be located in a hospital or clinical lab environment where Echocardiography is performed as a diagnostic aid in cardiology for the morphological and functional assessment of the heart. During a typical patient echocardiogram exam (referred to as a study), a sonographer or technician places the ultrasound imaging device 24 against the patient's chest to capture 2D echo images/videos of the heart to help diagnose the particular heart ailment. Measurements of the structure and blood flows are typically made using 2D slices of the heart and the position of the ultrasound imaging device 24 is varied during an echo exam to capture different anatomical sections of the heart from different viewpoints. The technician has the option of adding to these 2D echo images a waveform captured from various possible modalities including: continuous wave Doppler, m-mode, pulsed wave Doppler and pulsed wave tissue Doppler. The 2D images and Doppler waveform images may be saved as DICOM files. Although the type of modality is sometimes indicated in the metadata of the DICOM file, the 2D view is not.

The computer 14 may further include removable storage devices such as an optical disk 20 and/or a flash memory 22 and the like for storage of the echo images. In some embodiments, the removable storage devices may be used as an import source of echo images and related data structures into the internal image file archive 18, rather than or in addition to, the ultrasound imaging device 24. The removable storage devices may also be used as an archive for echocardiogram data stored in the database 16 and/or the image file archive 18.

In an advanced embodiment referred to as connected configuration 10B, the computer 14 may be connected through the network 26 and router 28 to other DICOM based devices, such as DICOM servers 30, network file share devices 32, Echo workstations 34, and/or cloud storage services 36 hosting DICOM files. In the connected configuration 10B, several possible interactions with the database 16 and the image file archive 18 are possible, as described below.

One possible interaction is to use the cloud storage services 36 as an internal archive. In case of very large archives consisting of large amounts of DICOM files, the computer 14 may not have sufficient storage to host all files and the echo workflow engine 12 may be configured to use external network storage of the cloud storage services 36 for file storage.

Another possible interaction is to use the cloud storage services 36 as an import source by i) selecting a DICOM file set or patient study, which includes the DICOM and Doppler waveforms images and patient data and examination information. The patient study may also be selected by a reserved DICOMDIR file instance, from which the patient, exams and image files are read.

Yet a further possible interaction is to use the DICOM servers 30, the network file share devices 32, echo workstations 34, and/or DICOM clients (of FIG. 1C) acting as DICOM servers (workstations with modalities CFind, CMove and CStore) in order to retrieve patients, exams and images by performing a CFind operation, followed by a CMove operation, to request the remote device to send the images resulting from the CFind operation.

Referring now to FIG. 1B, a handheld configuration 10C for the automated clinical workflow system is shown. In this embodiment, the computer 14 of FIG. 1A is implemented as a handheld device 14', such as a tablet or a mobile phone, connected to a wired or wireless portable ultrasound scanner probe 24' that transmits echo images to the handheld device 14'. In such embodiments, the echo workflow engine 12 may be implemented as an application executed by the handheld device 14'.

FIG. 1C illustrates a software as a service (SaaS) configuration 10D for the automated clinical workflow. In this embodiment, the echo workflow engine 12 is run on a server 40 that is in communication over the network 26 with a plurality of client devices 42. In this embodiment, the server 40 and the echo workflow engine 12 may be part of a third-party service that provides automated measurements and the diagnosis, prediction and prognosis of heart disease to client devices (e.g., hospital, clinic, or doctor computers) over the Internet. It should be understood that although the server 40 is shown as a single computer, it should be understood that the functions of server 40 may be distributed over more than one server. In an alternative embodiment, the server 40 and the echo workflow engine 12 of FIG. 1C may be implemented as a virtual entity whose functions are distributed over multiple client devices 42. Likewise, it should be understood that although the echo workflow engine 12 is shown as a single component in each embodiment, the functionality of the echo workflow engine 12 may be separated into a greater number of modules/components.

Conventionally, after a patient examination where echo images are captured stored, a clinician/technician goes through the DICOM files, manually annotates heart chambers and structures and takes measurements, which are presented in a report. In a follow up examination, a doctor will review the DICOM images and measurements, compare them to memorized guideline values and make a diagnosis. Such a process is reliant on the clinicians' training to recognize the view and make the appropriate measurements so that a proper diagnosis can be made. Such a process is error-prone and time consuming.

According to the disclosed embodiments, the echo workflow engine 12 mimics the standard clinical practice, processing DICOM files of a patient by using a combination of machine learning, image processing, and DICOM workflow techniques to derive clinical measurements, diagnose specific diseases, and prognosticate patient outcomes, as described below. While an automated solution to echo image interpretation using machine learning has been previously proposed, the solution only analyzes 2D echo images and not Doppler modality waveform images. The solution also mentions disease prediction, but only attempts to handle two diseases (hypertrophic cardiomyopathy and cardiac amyloidosis) and the control only compares normal patients to diseased patients.

The echo workflow engine 12 of the disclosed embodiments, however, improves on the automated solution by utilizing machine learning to automatically recognize and analyze not only 2D echo images but also Doppler modality waveform images. The echo workflow engine 12 is also capable of comparing patients having similar-looking heart diseases (rather than comparing normal patients to diseased patients), and automatically identifies additional diseases, including both heart failure with reduced ejection fraction (HFrEF) and heart failure with preserved ejection fraction (HFpEF). HFrEF is known as heart failure due to left ventricular systolic dysfunction or systolic heart failure and occurs when the ejection fraction is less than 40%. HFpEF is a form of congestive heart failure where in the amount of blood pumped from the heart's left ventricle with each beat (ejection fraction) is greater than 50%. Finally, unlike the proposed automated solution, the echo workflow engine 12 automatically generates a report with the results of the analysis for medical decision support.

Figure 2:
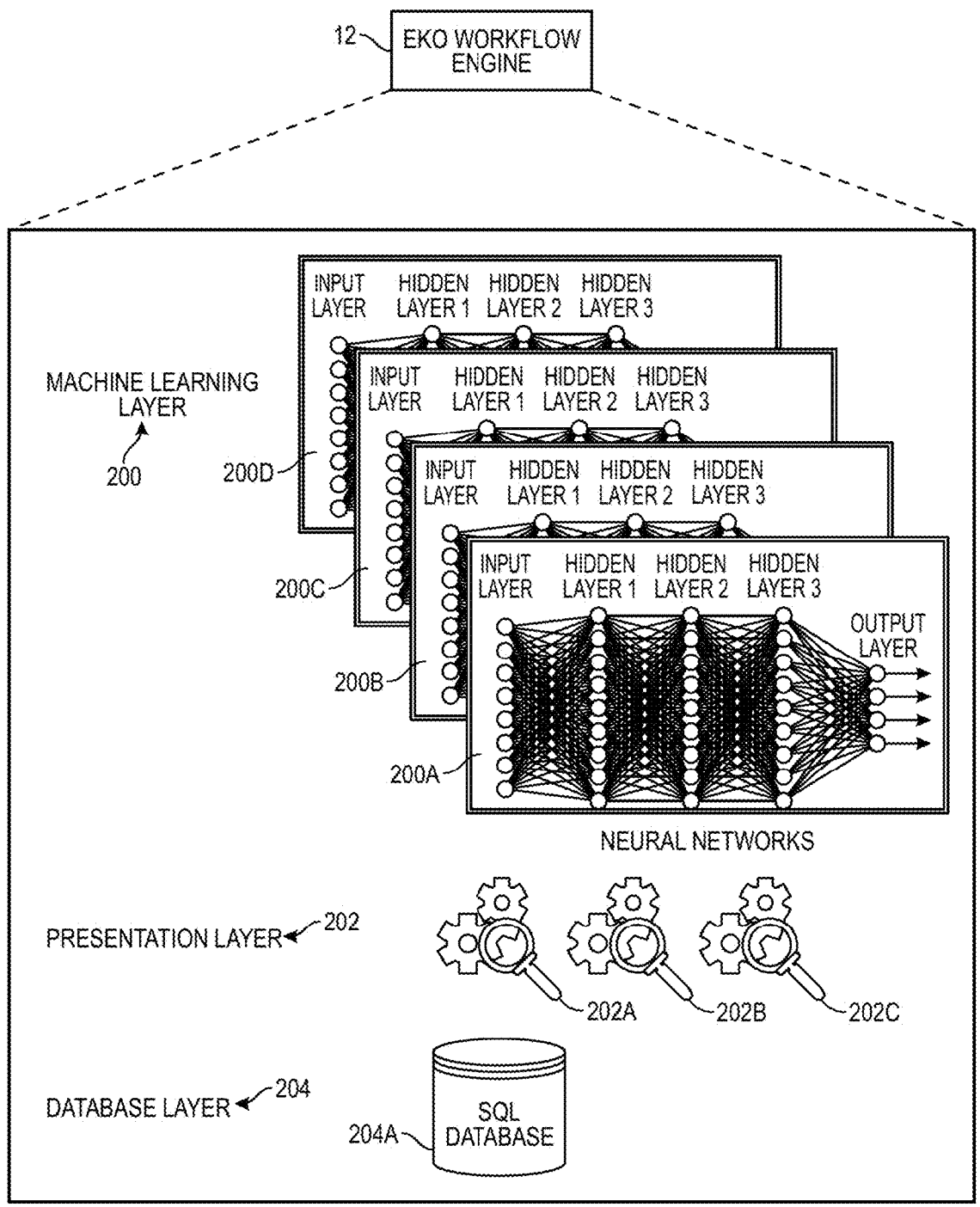
FIG. 2 illustrates architectural layers of the echo workflow engine.

FIG. 2 illustrates architectural layers of the echo workflow engine 12. In one embodiment, the echo workflow engine 12 may include a number of software components such as software servers or services that are packaged together in one software application. For example, the echo workflow engine 12 may include a machine learning layer 200, a presentation layer 202, and a database layer 204.

The machine learning layer 200 comprises several neural networks to process incoming echo images and corresponding metadata. The neural networks used in the machine learning layer may comprise a mixture of different classes or model types. In one embodiment, machine learning layer 200 utilizes a first neural network to classify 2D images by view type, and uses a second set of neural networks 200B to both extract features from Doppler modality images and to use the extracted features to classify the Doppler modality images by region (the neural networks used to extract features may be different than the neural network used to classify the images). The first neural network 200A and the second set of neural networks 200B may be implemented using convolutional neural network (CNN) and may be referred to as classification neural networks or CNNs.

Additionally, a third set of neural networks 200C, including adversarial networks, are employed for each classified 2D view type in order to segment the cardiac chambers in the 2D images and produce segmented 2D images. A fourth set of neural networks 200D are used for each classified Doppler modality region in order to segment the Doppler modality images to generate waveform traces. In additional embodiments, the machine learning layer 200 may further include a set of one or more prediction CNNs for disease prediction and optionally a set of one or more prognosis CNNs for disease prognosis (not shown). The third and fourth sets of neural networks 200C and 200D may be implemented using CNNs and may be referred to as segmentation neural networks or CNNs.

In machine learning, a CNN is a class of deep, feed-forward artificial neural network typically use for analyzing visual imagery. Each CNN comprises an input and an output layer, as well as multiple hidden layers. In neural networks, each node or neuron receives an input from some number of locations in the previous layer. Each neuron computes an output value by applying some function to the input values coming from the previous layer. The function that is applied to the input values is specified by a vector of weights and a bias (typically real numbers). Learning in a neural network progresses by making incremental adjustments to the biases and weights. The vector of weights and the bias are called a filter and represents some feature of the input (e.g., a particular shape).

The machine learning layer 200 operates in a training mode to train each of the CNNs 200A-200D prior to the echo workflow engine 12 being placed in an analysis mode to automatically recognize and analyze echo images in patient studies. In one embodiment, the CNNs 200A-200D may be trained to recognize and segment the various echo image views using thousands of echo images from an online public or private echocardiogram DICOM database.

The presentation layer 202 is used to format and present information to a user. In one embodiment, the presentation layer is written in HTML 5, Angular 4 and/or JavaScript. The presentation layer 202 may include a Windows Presentation Foundation (WPF) graphical subsystem 202A for implementing a light weight browser-based user interface that displays reports and allows a user (e.g., doctor/technician) to edit the reports. The presentation layer 202 may also include an image viewer 202B (e.g., a DICOM viewer) for viewing echo images, and a python server 202C for running the CNN algorithms and generating a file of the results in JavaScript Object Notation (JSON) format, for example.

The database layer 204 in one embodiment comprises a SQL database 204A and other external services that the system may use. The SQL database 204A stores patient study information for individual patient studies input to the system. In some embodiments, the database layer 204 may also include the image file archive 18 of FIG. 1.

Figure 3:
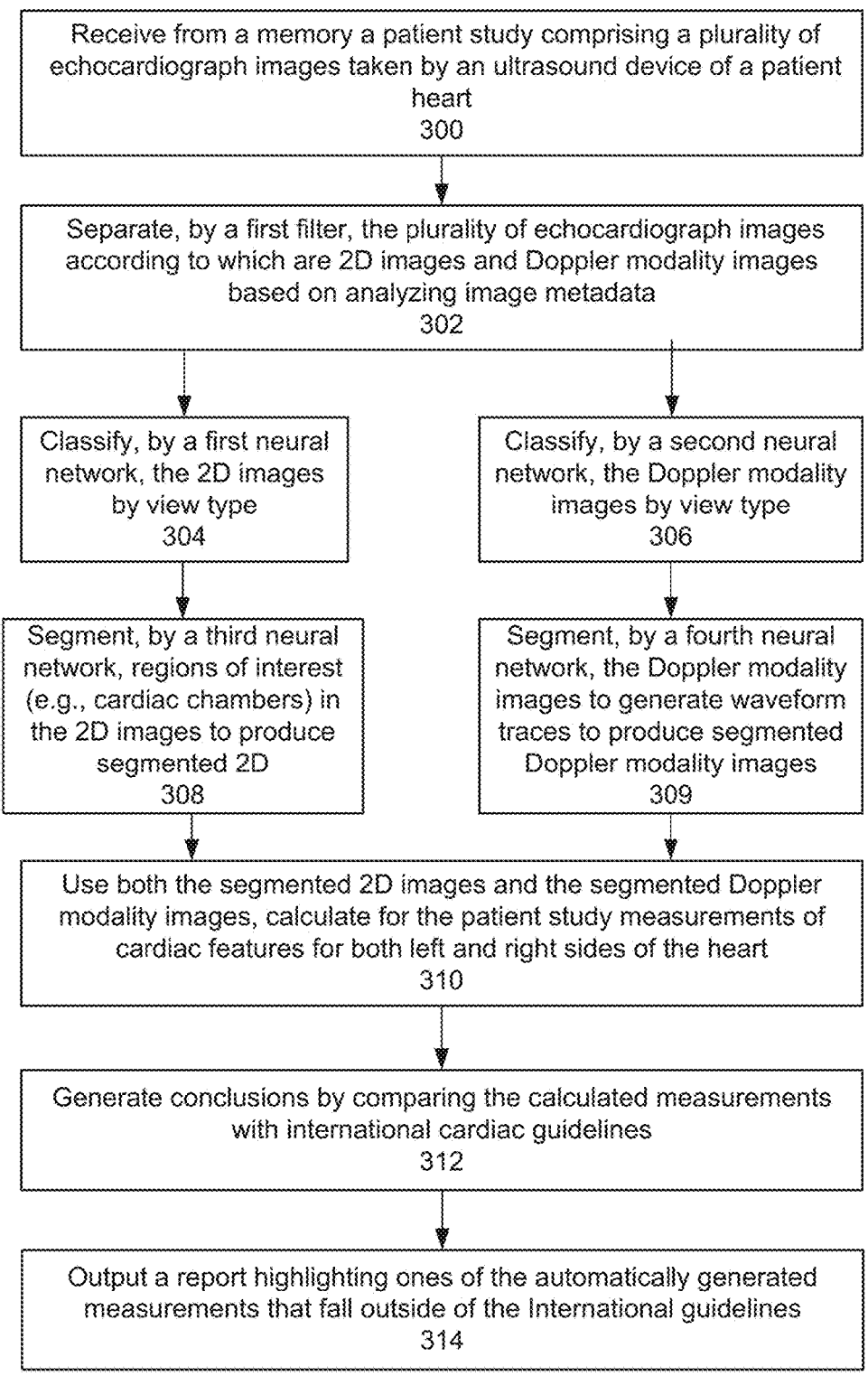
FIG. 3 is a flow diagram illustrating one embodiment of a process for performed by the echo workflow engine to automatically recognize and analyze both 2D and Doppler modality echo images to perform automated measurements and the diagnosis, prediction and prognosis of heart disease.

FIG. 3 is a flow diagram illustrating one embodiment of a process for performed by the echo workflow engine 12 to automatically recognize and analyze both 2D and Doppler modality echo images to perform automated measurements and the diagnosis, prediction and prognosis of heart disease. The process occurs once the echo workflow engine 12 is trained and placed in analysis mode.

The process may begin by the echo workflow engine 12 receiving from a memory one or more patient studies comprising a plurality of echocardiogram images taken by an ultrasound device of a patient organ, such as a heart (block 300). In one embodiment, the patient study may include 70-90 images and videos.

A first module of the echo workflow engine 12 may be used to operate as a filter to separate the plurality of echocardiogram images according to 2D images and Doppler modality images based on analyzing image metadata (block 302). The first module analyzes the DICOM tags, or metadata, incorporated in the image, and runs an algorithm based upon the tag information to distinguish between 2D and modality images, and then separate the modality images into either pulse wave, continuous wave, PWTDI or m-mode groupings. A second module of the echo workflow engine 12 may perform color flow analysis on extracted pixel data using a combination of analyzing both DICOM tags/metadata and color content within the images, to separate views that contain color from those that do not. A third module then anonymizes the data by removing metatags that contain personal information and cropping the images to exclude any identifying information. A fourth module then extracts the pixel data from the images and converts the pixel data to numpy arrays for further processing.

Because sonographers do not label the view types in the echo images, one or more of neural networks are used classify the echo images by view type. In one embodiment, a first neural network is used by the echo workflow engine 12 to classify the 2D images by view type (block 304); and a second set of neural networks is used by the echo workflow engine 12 to extract the features from Doppler modality images and to use the extracted features to classify the Doppler modality images by region (block 306). As shown, the processing of 2D images is separate from the processing of Doppler modality images. In one embodiment, the first neural network and the second set of neural networks may implemented using the set of classification convolutional neural networks (CNNs) 200A. In one specific embodiment, a five class CNN may be used to classify the 2D images by view type and an 11 class CNN may be used to classify the Doppler modality images by region. Each of the neural networks, and classifying by view type, can use a majority voting scheme to determine the optimal answer. For example a video can be divided into still image frames, and each frame may be given a classification label, i.e., of a vote, and the classification label receiving the most votes is applied to classify the video.

In one embodiment, the echo workflow engine 12 is trained to classify many different view types. For example, the echo workflow engine 12 may classify at least 11 different view types including parasternal long axis (FLAX), apical 2-, 3-, and 4-chamber (A2C, A3C, and A4C), A4C plus pulse wave of the mitral valve, A4C plus pulse wave tissue Doppler on the septal side, A4C plus pulse wave tissue Doppler on the lateral side, A4C plus pulse wave tissue Doppler on the tricuspid side, A5C plus continuous wave of the aortic valve, A4C+Mmode (TrV), A5C+PW (LVOT).

Based on the classified images, a third set of neural networks is used by the echo workflow engine 12 to segment regions of interest (e.g., cardiac chambers) in the 2D images to produce annotated or segmented 2D images (block 308). A fourth set of neural networks is used by the echo workflow engine 12 for each classified Doppler modality region to generate waveform traces and to generate annotated or segmented Doppler modality images (block 309). The process of segmentation includes determining locations where each of the cardiac chambers begin and end to generate outlines of structures of the heart (e.g., cardiac chambers) depicted in each image and/or video. Segmentation can also be used to trace the outline of the waveform depicting the velocity of blood flow in a Doppler modality. In one embodiment, the third and fourth sets of neural networks maybe referred to as segmentation neural networks and my comprise the set of segmentation CNNs 200B and 200C. The choice of segmentation CNN used is determined by the view type of the image, which makes the prior correct classification of view type a crucial step. In a further embodiment, once regions of interest are segmented, a separate neural network can be used to smooth outlines of the segmentations.

As will be explained further below, the segmentation CNNs may be trained from hand-labeled real images or artificial images generated by general adversarial networks (GANs).

Using both the segmented 2D images and the segmented Doppler modality images, the echo workflow engine 12 calculates for the patient study, measurements of cardiac features for both left and right sides of the heart (block 310).

The echo workflow engine 12 then generates conclusions by comparing the calculated measurements with international cardiac guidelines (block 312). The echo workflow engine 12 further outputs at least one report to a user highlighting ones of the calculated measurements that fall outside of the International guidelines (block 314). In one embodiment, two reports are generated and output: the first report is a list of the calculated values for each measurement with the highest confidence as determined by a rules based engine, highlighting values among the calculated measurements that fall outside of the International guidelines; and the second report is a comprehensive list of all measurements calculated on every image frame of every video, in every view, generating large volumes of data. All report data and extracted pixel data may be stored in a structured database to enable machine learning and predictive analytics on images that previously lacked the quantification and labelling necessary for such analysis. The structured database may be exported to a cloud based server or may remain on premises (e.g., of the lab owning the images) and can be connected to remotely. By connecting these data sources into a single network, disease prediction algorithms can be progressively trained across multiple network nodes, and validated in distinct patient cohorts. In one embodiment, the reports may be electronically displayed to a doctor and/or a patient on a display of an electronic device and/or as a paper report. In some embodiments, the electronic reports may be editable by the user per rule or role based permissions, e.g., a cardiologist may be allowed to modify the report, but a patient may have only view privileges.

Figure 4A:
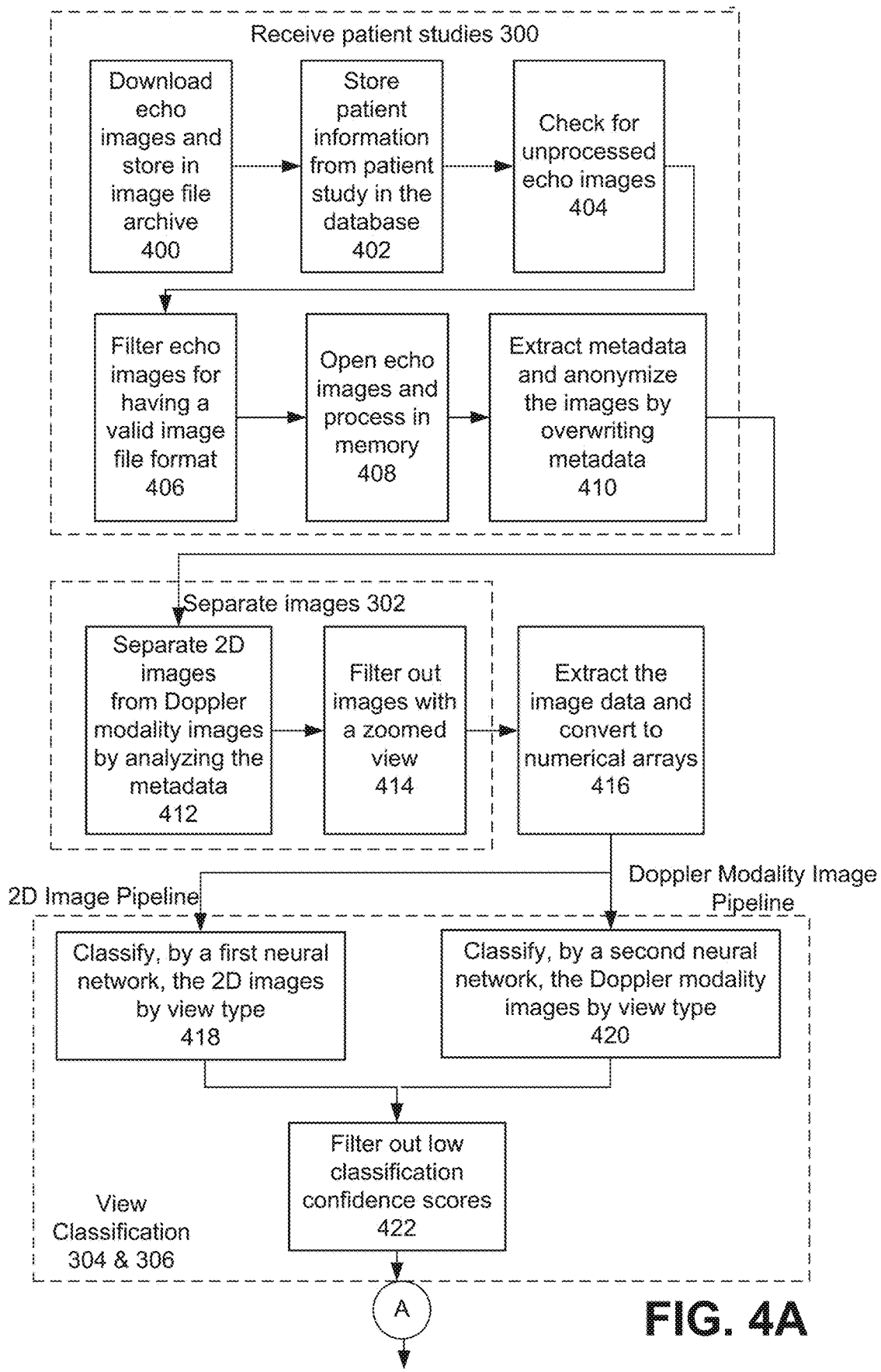
FIG. 4A is a flow diagram illustrating details of the process for automatically recognizing and analyze both 2D and Doppler modality echo images to perform automated measurements and the diagnosis, prediction and prognosis of heart disease according to one embodiment.
Figure 4A:
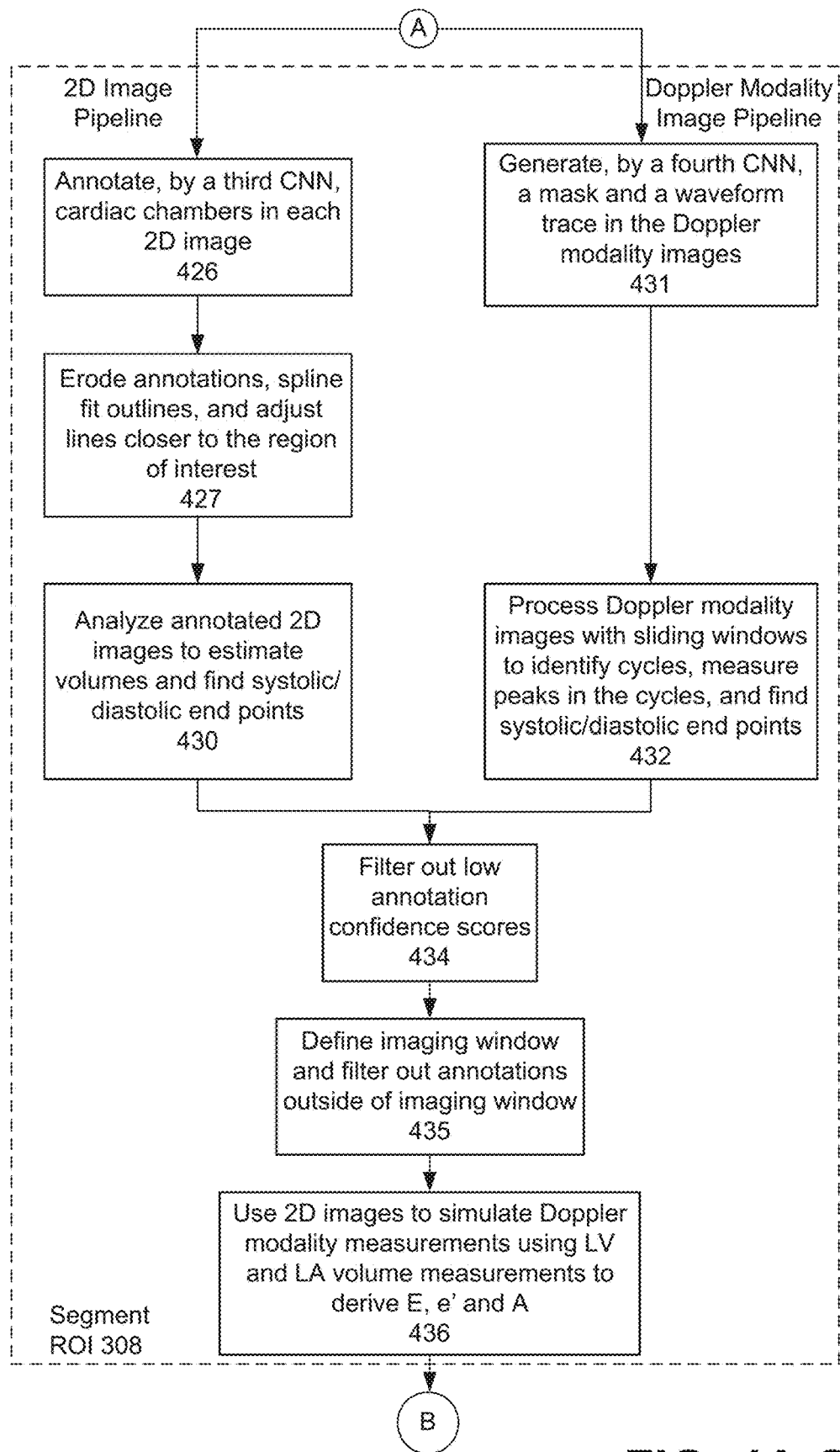
Figure 4A:
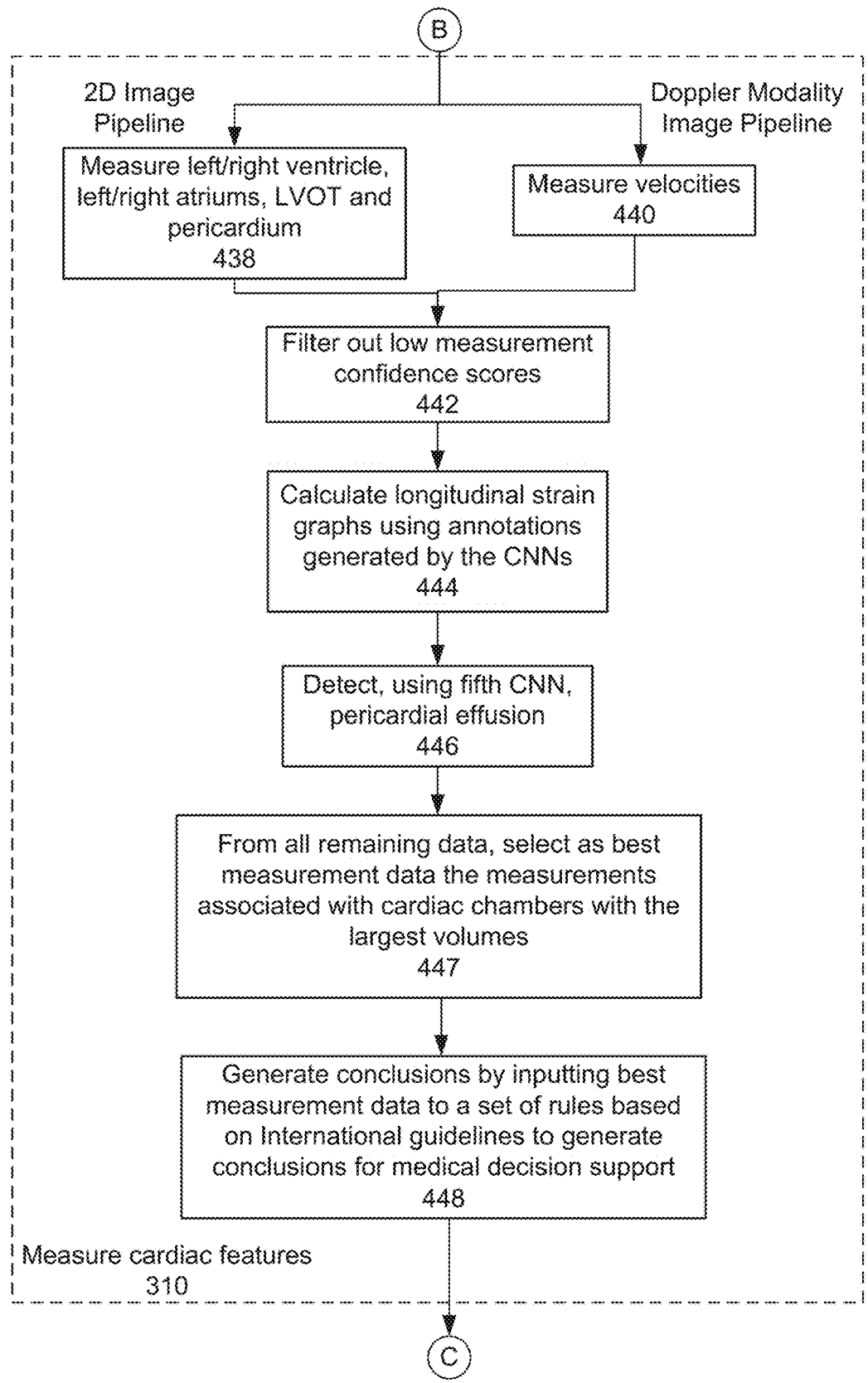
Figure 4A:
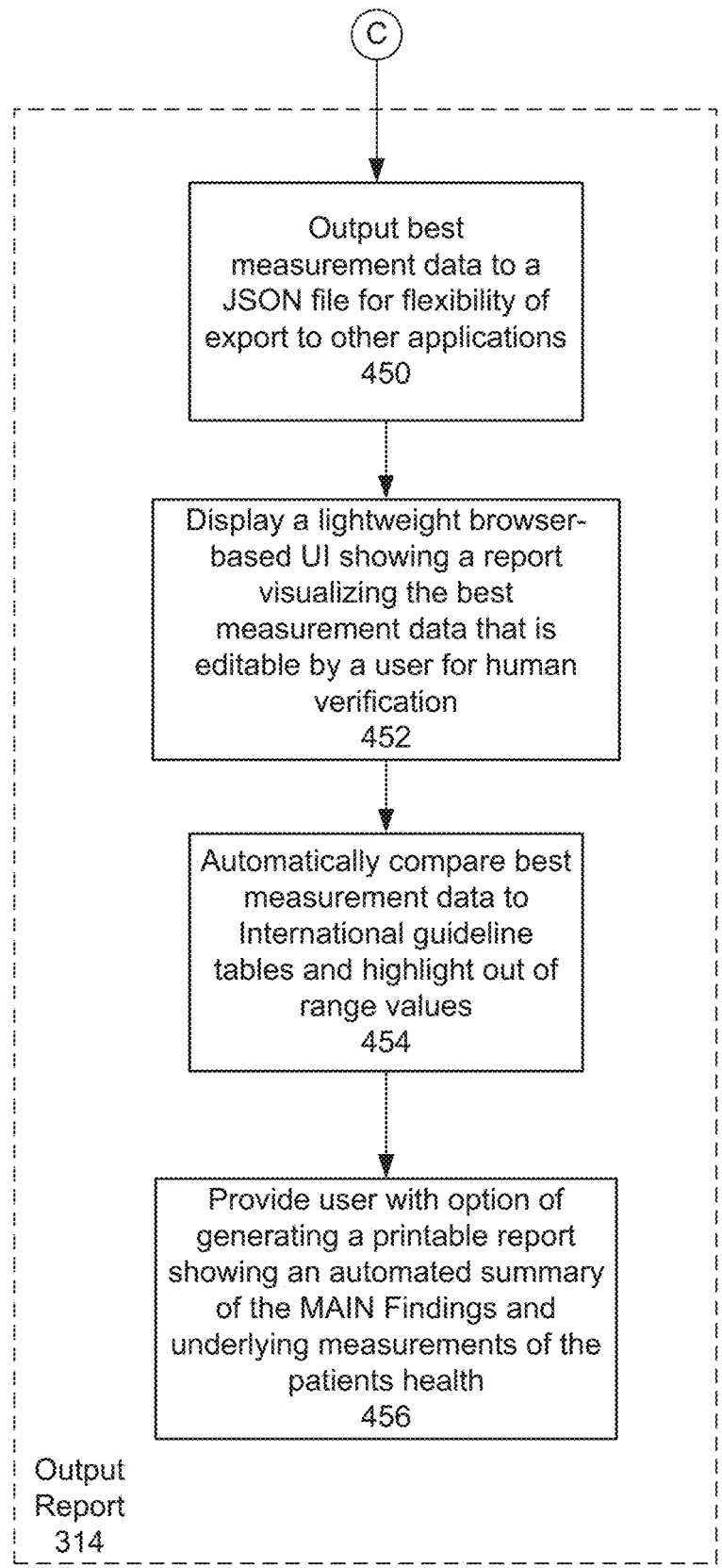

FIG. 4A is a flow diagram illustrating further details of the process for automatically recognizing and analyze both 2D and Doppler modality echo images to perform automated measurements and the diagnosis, prediction and prognosis of heart disease according to one embodiment.

The process may begin with receiving one or more patient studies (FIG. 3 block 300), which comprises blocks 400-4010. In one embodiment, echo images from each of the patient studies are automatically downloaded into the image file archive 18 (block 400). The echo images may be received from a local or remote storage source of the computer 14. The local storage sources may include internal/external storage of the computer 14 including removable storage devices. The remote storage sources may include the ultrasound imaging device 24, the DICOM servers 30, the network file share devices 32, the echo workstations 34, and/or the cloud storage services 36 (see FIG. 1). In one embodiment, the echo workflow engine 12 includes functions for operating as a picture archiving and communication server (PACS), which is capable of handling images from multiple modalities (source machine types, one of which is the ultrasound imaging device 24). The echo workflow engine 12 uses PACS to download and store the echo images into the image file archive 18 and provides the echo workflow engine 12 with access to the echo images during the automated workflow. The format for PACS image storage and transfer is DICOM (Digital Imaging and Communications in Medicine).

Patient information from each of the patient studies is extracted and stored in the database 16 (block 402). Non-image patient data may include metadata embedded within the DICOM images and/or scanned documents, which may be incorporated using consumer industry standard formats such as PDF (Portable Document Format), once encapsulated in DICOM. In one embodiment, received patient studies are placed in a processing queue for future processing, and during the processing of each patient study, the echo workflow engine 12 queues and checks for unprocessed echo images (block 404). The echo workflow engine 12 monitors the status of patient studies, and keeps track of them in a queue to determine which have been processed and which are still pending. In one embodiment, prioritization of the patient studies in the queue may be configured by a user. For example, the patient studies may be prioritized in the queue for processing according to the date of the echo exam, the time of receipt of the patient study or by estimated severity of the patient's heart disease.

Any unprocessed echo images are then filtered for having a valid DICOM image format and non DICOM files in an echo study are discarded (block 406). In one embodiment, the echo images are filtered for having a particular type of format, for example, a valid DICOM file format, and any other file formats may be ignored. Filtering the echo images for having a valid image file format enhances the reliability of the echo workflow engine 12 by rejecting invalid DICOM images for processing.

Any unprocessed valid echo images are then opened and processed in the memory of the computer 14 (block 408). Opening of the echo images for the patient study in memory of the computer 14 is done to enhance processing speed by echo workflow engine 12. This is in contrast to an approach of opening the echo files as sub-processes, saving the echo files to disk, and then reopening each echo image during processing, which could significantly slow processing speed.

The echo workflow engine 12 then extracts and stores the metadata from the echo images and then anonymizes the images by blacking out the images and overwriting the metadata in order to protect patient data privacy by covering personal information written on the image (block 410). As an example, DICOM formatted image files include metadata referred to as DICOM tags that may be used to store a wide variety of information such as patient information, Doctor information, ultrasound manufacture information, study information, and so on. In one embodiment, the extracted metadata may be stored in the database 16 and the metadata in image files is over written for privacy.

After receipt and processing of the patient studies, the echo workflow engine 12 separates 2D images from Doppler modality images so the two different image types can be processed by different pipeline flows, described below. In one embodiment, the separating of the images (FIG. 3 block 302) may comprise blocks 412-414. First, the 2D images are separated from the Doppler modality images by analyzing the metadata (block 412).

Figure 5A:
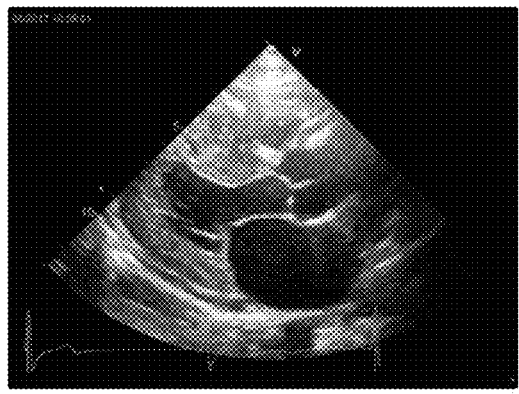
FIG. 5A is diagram illustrating an example 2D echo image.
Figure 5B:
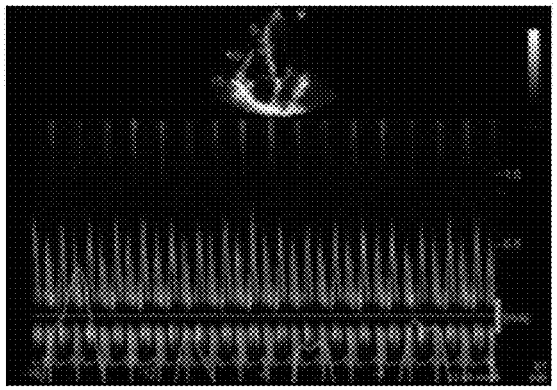
FIG. 5B is diagram illustrating an example Doppler modality image.
Figure 6A:
FIGS. 6A-6K are diagrams illustrating some example view types automatically classified by the echo workflow engine.
Figure 6B:
Figure 6C:
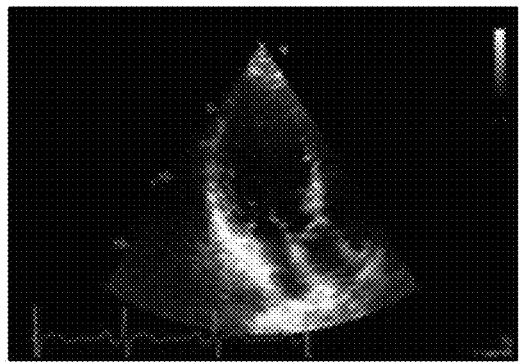
Figure 6D:
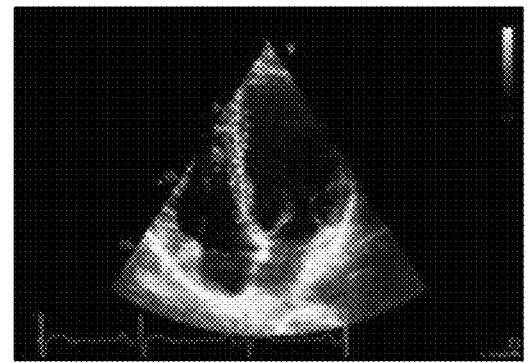
Figure 6E:
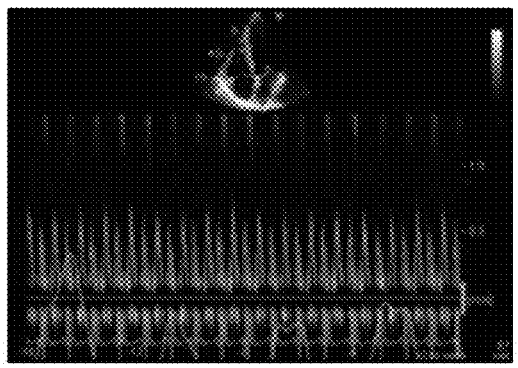
Figure 6F:
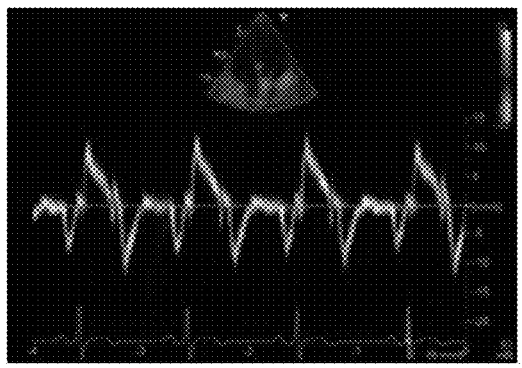
Figure 6G:
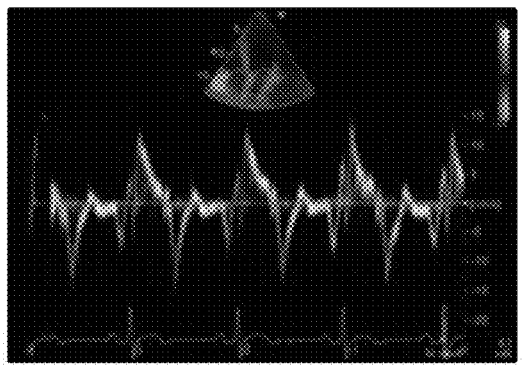
Figure 6H:
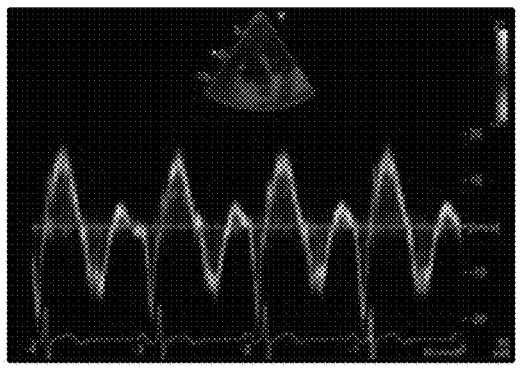
Figure 6I:
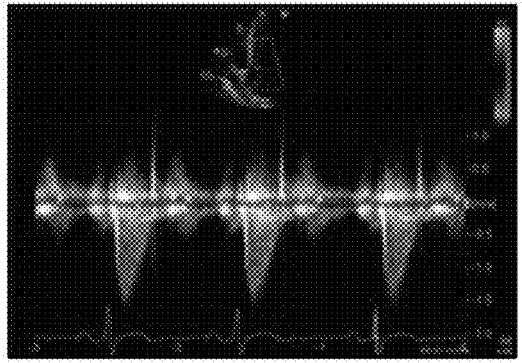
Figure 6J:
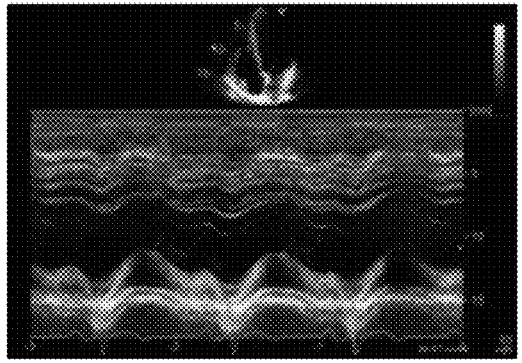
Figure 6K:
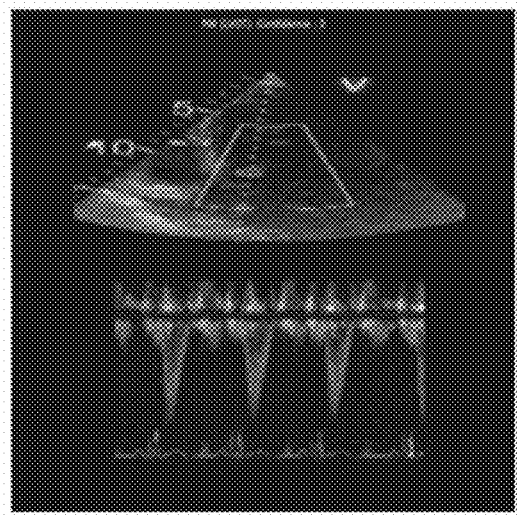

FIGS. 5A and 5B are diagrams illustrating an example 2D echo image 500 and an example Doppler modality image 502 including a waveform, respectively. The echo workflow engine 12 may determine the image type by examining metadata/DICOM tags. In one embodiment, information within the DICOM tags may be extracted in order to group the images into one of the following four classes: 2D only, pulsed-wave (PW), continuous wave (CW), and m-mode. Similarly, the transducer frequency of the ultrasound imaging device 24 in the metadata may be used to further separate some of the PW images into a fifth class: pulsed-wave tissue doppler imaging (PWTDI).

Referring again to FIG. 4A, the echo workflow engine 12 may also filter out images with a zoomed view, which may also be determined by analyzing the metadata (block 414). Any of the echo images that has been zoomed during image capture are not processed through the pipeline because when zooming, useful information is necessarily left out of the image, meaning the original image would have to be referenced for the missing data, which is a duplication of effort that slows processing speed. Accordingly, rather than potentially slowing the process in such a manner, the echo workflow engine 12 filters out or discards the zoomed images to save processing time. In an alternative embodiment, filtering out zoomed images in block 414 may be performed prior to separating the images in block 412.

After separating the 2D images from the Doppler modality images, the echo workflow engine 12 extracts and converts the image data from each echo image into numerical arrays 416 (block 416). For the echo images that are 2D only, the pixel data comprises a series of image frames played in sequence to create a video. Because the image frames are unlabeled, the view angle needs to be determined. For the Doppler modality images that include waveform modalities, there are two images in the DICOM file that may be used for subsequent view identification, a waveform image and an echo image of the heart. The pixel data is extracted from the DICOM file and tags in the DICOM file determine the coordinates to crop the images. The cropped pixel data is stored in numerical arrays for further processing. In one embodiment, blocks 412, 414 and 416 may correspond to the separating images block 302 of FIG. 3.

After separating images, the echo workflow engine 12 attempts to classify each of the echo images by view type. In one embodiment, view classification (FIG. 3 blocks 304 and 306) correspond to blocks 418-422.

According to the disclosed embodiments, the echo workflow engine 12 attempts to classify each of the echo images by view type by utilizing parallel pipeline flows. The parallel pipeline includes a 2D image pipeline and a Doppler modality image pipeline. The 2D pipeline flow begins by classifying, by a first CNN, the 2D images by view type (block 418), corresponding to block 304 from FIG. 3. The Doppler modality image pipeline flow begins by classifying, by a second CNN, the Doppler modality images by view type (block 420), corresponding to block 306 from FIG. 3.

FIGS. 6A-6K are diagrams illustrating some example view types automatically classified by the echo workflow engine 12. As stated previously, example view types may include parasternal long axis (PLAX), apical 2-, 3-, and 4-chamber (A2C, A3C, and A4C), A4C plus pulse wave of the mitral valve, A4C plus pulse wave tissue Doppler on the septal side, A4C plus pulse wave tissue Doppler on the lateral side, A4C plus pulse wave tissue Doppler on the tricuspid side, A5C plus continuous wave of the aortic valve, A4C+Mmode (TrV), A5C+PW (LVOT).

Referring again to FIG. 4A, in one embodiment, 2D image classification is performed as follows. If the DICOM file contains video frames from a 2D view, only a small subset of the video frames are analyzed to determine 2D view classification for more efficient processing. In one embodiment, the subset of the video frames may range approximately 8-12 video frames, but preferably 10 frames are input into one of the CNNs 200A trained for 2D to determine the actual view. In an alternative embodiment, subset a video frames may be randomly selected from the video file. In one embodiment, the CNNs 200A classify each of the analyzed video frames as one of: A2C, A3C, A4C, ASC, PLAX Modified, PLAX, PSAX AoV level, PSAX Mid-level, Subcostal Ao, Subcostal Hep vein, Subcostal IVC, Subcostal LAX, Subcostal SAX, Suprasternal and Other.

Doppler modality images comprise two images, an echocardiogram image of the heart and a corresponding waveform, both of which are extracted from the echo file for image processing. In one embodiment, Doppler modality image classification of continuous wave (CW), pulsed-wave (PW), and M-mode images is performed as follows. If the DICOM file contains a waveform modality (CW, PW, PWTDI, M-mode), the two extracted images are input to one of the CNNs 200A trained for CW, PW, PWTDI and M-mode view classification to further classify the echo images as one of: CW (AoV), CW (TrV), CW Other, PW (LVOT), PW (MV), PW Other, PWTDI (lateral), PWTDI (septal), PWTDI (tricuspid), M-mode (TrV) and M-mode Other.

There are many more potential classifications available for modalities, but the present embodiments strategically select the classes above, while grouping the remaining potential classes into "Other", in order to maximize processing efficiency, while identifying the most clinically important images for further processing and quantification. Customization of the CNNs 200A occurs in the desired number of layers used and the quantity of filters within each layer. During the training phase, the correct size of the CNNs may be determined through repeated training and adjustments until optimal performance levels are reached.

During view classification, the echo workflow engine 12 maintains classification confidence scores that indicate a confidence level that the view classifications are correct. The echo workflow engine 12 filters out the echo images having classification confidence scores that fail to meet a threshold, i.e., low classification confidence scores (block 422). Multiple algorithms may be employed to derive classification confidence scores depending upon the view in question. Anomalies detected in cardiac structure annotations, image quality, cardiac cycles detected and the presence of image artifacts may all serve to decrease the classification confidence score and discard an echo image out of the automated echo workflow.

With respect to the confidence scores, the echo workflow engine 12 generates and analyzes several different types of confidence scores at different stages of processing, including classification, annotation, and measurements (e.g., blocks 422, 434 and 442). For example, poor quality annotations or classifications, which may be due to substandard image quality, are filtered out by filtering the classification confidence scores. In another example, in a patient study the same view may be acquired more than once, in which case the best measurements are chosen by filtering out low measurement confidence scores as described further below in block 442. Any data having a confidence score that meets a predetermined threshold continues through the workflow. Should there be a duplication of measurements both with high confidence, the most clinically relevant measurement may be chosen.

Next, the echo workflow engine 12 performs image segmentation to define regions of interest (ROI). In computer vision, image segmentation is the process of partitioning a digital image into multiple segments (sets of pixels) to locate and boundaries (lines, curves, and the like) of objects. Typically, annotations are a series of boundary lines overlaying overlaid on the image to highlight segment boundaries/edges. In one embodiment, the segmentation to define ROI (FIG. 3 block 308) corresponds to blocks 426-436.

In one embodiment, the 2D image pipeline annotates, by a third CNN, regions of interests, such as cardiac chambers in the 2D images, to produce annotated 2D images (block 426). An annotation post process then erodes the annotations to reduce their dimensions, spline fits outlines of cardiac structures and adjusts locations of the boundary lines closer to the region of interest (ROIs) (block 427). The 2D image pipeline continues with analyzing the ROIs (e.g., cardiac chambers) in the annotated 2D images to estimate volumes and determine key points in the cardiac cycle by finding systolic/diastolic end points (block 430). For 2D only views, measurements are taken at the systolic or diastolic phase of the cardiac cycle, i.e. when the left ventricle reaches the smallest volume (systole) or the largest volume (diastole). From the 2D video images, it must be determined which end points are systolic and which are diastolic based on the size of the estimated volumes of the left ventricle. For example, a significantly large left ventricle may indicate a dystonic end point, while a significantly small volume may indicate a systolic end point. Every video frame is annotated and the volume of the left ventricle is calculated throughout the whole cardiac cycle. The frames with minimum and maximum volumes are detected with a peak detection algorithm.

The Doppler modality pipeline analyzes the Doppler modality images and generates, by a fourth CNN, a mask and a waveform trace in the Doppler modality images to produce annotated Doppler modality images (block 431).

Figure 7:
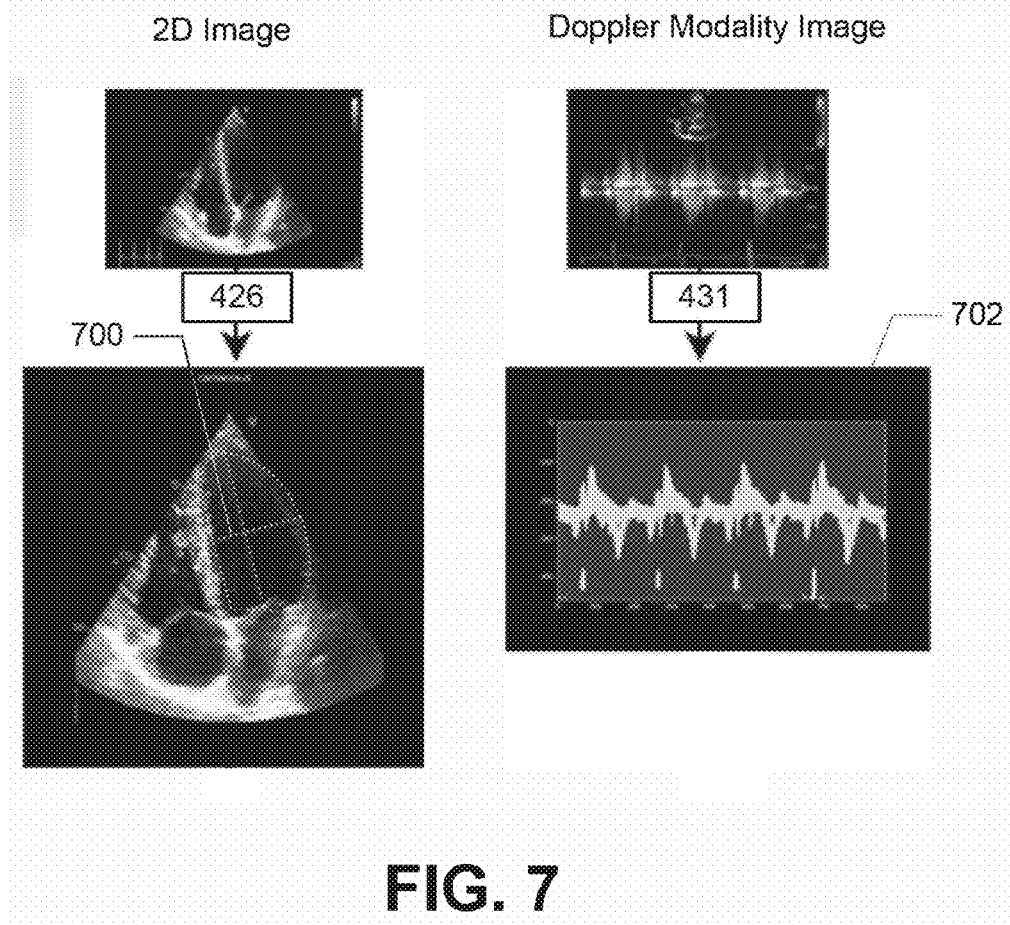
FIG. 7 is a diagram illustrating an example 2D image segmented to produce annotations indicating cardiac chambers, and an example Doppler modality image segmented to produce a mask and trace waveform

FIG. 7 is a diagram illustrating an example 2D image segmented in block 426 to produce annotations 700 indicating cardiac chambers, and an example Doppler modality image segmented in block 431 to produce a mask and waveform trace 702.

In one embodiment, the third and fourth CNNs may correspond to segmentation CNNs 200B. In one embodiment, each of the CNNs 200B used to segment the 2D images and Doppler modality images may be implemented as U-Net CNN, which is convolutional neural network developed for biomedical image segmentation. Multiple U-Nets may be used. For example, for 2D images, a first U-Net CNN can be trained to annotate ventricles and atria of the heart from the A2C, A3C, A4C views. A second U-net CNN can be trained to annotate the chambers in the PLAX views. For M-mode views, a third U-Net CNN can be trained to segment the waveform, remove small pieces of the segments to find likely candidates for the region of interest, and then reconnect the segments to provide a full trace of the movement of the mitral valve. For CW views, a fourth U-net CNN can be trained to annotate and trace blood flow. For PW views, a fifth U-net CNN trained to annotate and trace the blood flow. For PWTDI views, a sixth U-net CNN can be trained to annotate and trace movement of the tissues structures (lateral/septal/tricuspid valve).

Referring again to FIG. 4A, the Doppler modality pipeline continues by processing the annotated Doppler modality images with a sliding window to identify cycles, peaks are measured in the cycles, and key points in the cardiac cycle are determined by finding systolic/diastolic end points (block 432). Typically a Doppler modality video may capture three heart cycles and the sliding window is adjusted in size to block out two of the cycles so that only one selected cycle is analyzed. Within the selected cycle, the sliding window is used to identify cycles, peaks are measured in the cycles, and key points in the cardiac cycle are determined by finding systolic/diastolic end points.

Figure 8A:
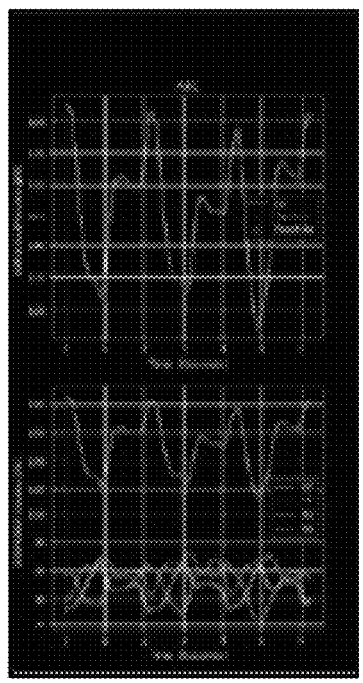
FIGS. 8A and 8B are diagrams illustrating examples of finding systolic/diastolic end points.
Figure 8B:
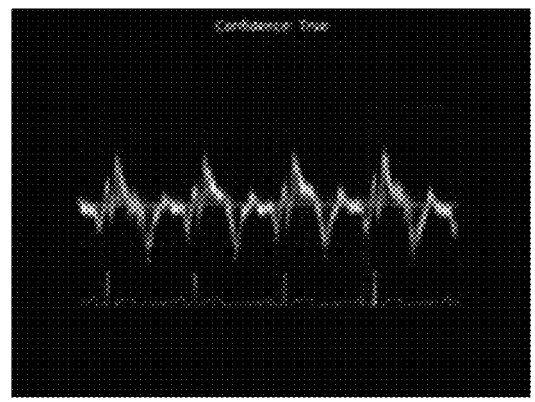

FIGS. 8A and 8B are diagrams illustrating examples of finding systolic/diastolic end points in the cardiac cycle, for both 2D and Doppler modalities, respectively, which are key points in order to take accurate cardiac measurements Referring again to FIG. 4A, in one embodiment, the echo workflow engine 12 maintains annotation confidence scores corresponding to the estimated volumes, systolic/diastolic end points, identified cycles and measured peaks. The echo workflow engine 12 filters out annotated images having annotation confidence scores that fail to meet a threshold, i.e., low annotated confidence scores (block 434). Examples of low confidence annotations may include annotated images having one or more of: excessively small areas/volumes, sudden width changes, out of proportion sectors, partial heart cycles, and insufficient heart cycles.

After images having low annotation confidence scores are filtered out, the echo workflow engine 12 defines an imaging window for each image, and filters out annotations that lie outside of the imaging window (block 435).

Figure 9A:
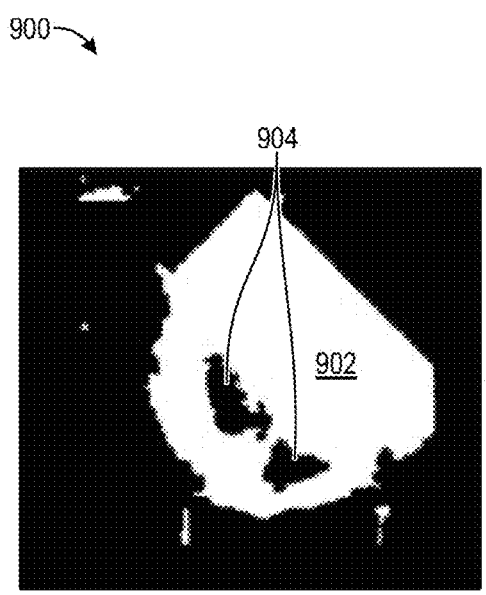
FIGS. 9A and 9B are diagrams illustrating processing of an imaging window in a 2D echo image and the automated detection of out of sector annotations.
Figure 9B:
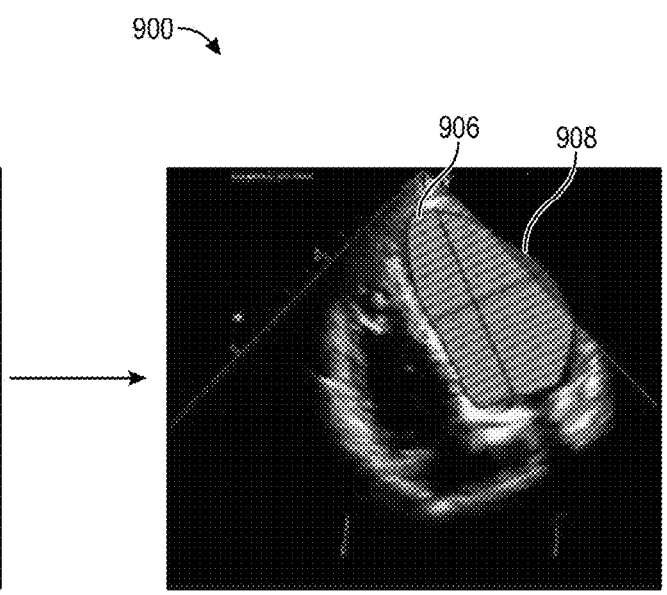

FIGS. 9A and 9B are diagrams illustrating processing of an imaging window in a 2D echo image 900. In FIG. 9A, a shaded ROI 902 is shown having unshaded regions or holes 904 therein. Open CV morphology transformations are used to fill the holes 904 inside the ROI, as shown in In FIG. 9B. Thereafter, a Hough line transformation may be used to find an imaging window border 906. As is well known, a Hough transform is a feature extraction technique used in digital image processing to find imperfect instances of objects within a certain class of shapes. After an imaging window border is are found, a pixel account of annotations beyond the imaging window border is made. Annotations 908 with a significant number of pixels outside the border of the imaging window are then discarded.

Referring again to FIG. 4A, in the handheld configuration for the automated clinical workflow system 10C (See FIG. 1B), the patient studies may not include Doppler modality images. According to a further aspect, the disclosed embodiments accommodate for such handheld configurations by using the 2D images to simulate Doppler modality measurements by using Left Ventricular (LV) and Left Atrial (LA) volume measurements to derive E, e' and A (e.g., early and late diastolic transmittal flow and early/mean diastolic tissue velocity) measurements (block 436). In one embodiment, simulating the Doppler modality measurements may be optional and may be invoked based on a software setting indicating the presence of a handheld configuration and/or absence of Doppler modality images for the current patient study.

Referring again to FIG. 4A, in one embodiment, once cardiac features are annotated during segmentation, the cardiac features are then measured during a measurement process (block 310 of FIG. 3), which in one embodiment may comprises block 438-448. The process of measuring cardiac features may begin by quantifying a plurality of measurements using the annotations. First, the 2D pipeline measures for the 2D images left/right ventricle, left/right atriums, left ventricular outflow (LVOT) and pericardium (block 438). For the Doppler modality images, the Doppler modality image pipeline measures blood flow velocities (block 440).

More specifically, for A2C, A3C, A4C, and A5C image views, volumetric measurements of chamber size are conducted on the systolic and diastolic frames of the video, and image processing techniques mimic a trained clinician at measuring the volume using the method of disks (MOD). For 2D Plax, PSAX (mid level), PSAX (AoV level), Subcostal, Suprasternal and IVC image views, linear measurements of chamber size and inter-chamber distances are conducted on the systolic and diastolic frames of the video using image processing techniques to mimic the trained clinician. For M-mode image views, from the annotated segments of the movement of the Tricuspidvalve, a center line is extracted and smoothed, and then the peaks and valleys are measured in order to determine the minimum and maximum deviations over the cardiac cycle. For PW image views, from the annotations of the blood flow, a mask is created to isolate parts of the waveform. A sliding window is then run across the trace to identify one full heart cycle, in combination with heart rate data from the DICOM tags, to use as a template. This template is then used to identify all other heart cycles in the image. Peak detection is then performed on each cycle and then run through an algorithm to identify which part of the heart cycle each peak represents. For CW image views, from the annotations of the trace of the blood flow, curve fitting is performed on the annotation to then quantify the desired measurements. For PWTDI image views, from the annotations of the movement of the tissue, a mask is created to isolate parts of the waveform. A sliding window is then run across the trace to identify one full heart cycle, in combination with heart rate data from the DICOM tags, to use as a template. This template is then used to identify all other heart cycles in the image. Peak detection is then performed on each cycle and then run through an algorithm to identify which part of the heart cycle each peak represents.

FIGS. 10A and 10B are diagrams graphically illustrating structural measurements automatically generated from annotations of cardiac chambers in a 2D image, and velocity measurements automatically generated from annotations of waveforms in a Doppler modality, respectively.

The measurement table below list the measurements that may be compiled by the echo workflow engine 12 according to one embodiment.

Measurement Table

| Measurement Name | Measurement Description |
| --- | --- |
| LAESV MOD A2C | Left Atrial End Systolic Volume in A2C calculation based on Method Of Discs |
| LAESVi MOD A2C | Left Atrial End Systolic Volume in A2C calculation based on Method Of Discs indexed to BSA |
| LAL A2C | Left Atrial End Sysolic Length measured in A2C |
| LVEDV MOD A2C | Left Ventricular End Diastolic Volume in A2C calculation based on Method Of Discs |
| LVEDVi MOD A2C | Left Ventricular End Diastolic Volume in A2C calculation based on Method Of Discs indexed to BSA |
| LVEF MOD A2C | Left Ventricular Ejection Fraction in A2C based on Method Of Discs |

-continued

| Measurement Name | Measurement Description |
| --- | --- |
| LVESV MOD A2C | Left Ventricular End Systolic Volume in A2C calculation based on Method Of Discs |
| LVESVi MOD A2C | Left Ventricular End Systolic Volume in A2C calculation based on Method Of Discs indexed to BSA |
| LV length A2C | Left Ventricular Length measured in A2C |
| LAESV MOD A4C | Left Atrial End Systolic Volume in A4C calculation based on Method Of Discs |
| LAESVi MOD A4C | Left Atrial End Systolic Volume in A4C calculation based on Method Of Discs indexed to BSA |
| LAL A4C | Left Atrial End Systolic Length measured in A4C |
| LAW A4C | Left Atrial End Systolic Width measurement in A4C |
| LA area A4C | Left Atrial Area measured in A4C |
| LAESV A-L A4C | Left Atrial End Systolic Volume in A4C calculation based on Area-Length method |
| LVEDV MOD A4C | Left Ventricular End Diastolic Volume in A4C calculation based on Method Of Discs |
| LVEDVi MOD A4C | Left Ventricular End Diastolic Volume in A4C calculation based on Method Of Discs indexed to BSA |
| LVEF MOD A4C | Left Ventricular Ejection Fraction in A4C based on Method Of Discs |
| LVESV MOD A4C | Left Ventricular End Systolic Volume in A4C calculation based on Method Of Discs |
| LVESVi MOD A4C | Left Ventricular End Systolic Volume in A4C calculation based on Method Of Discs indexed to BSA |
| LV length A4C | Left Ventricular Length measured in A4C |
| LVAd A4C | Left Ventricular Area measured at end diastole in A4C |
| TAPSE | Tricuspid Annular Plane Systolic Excursion |
| DecT | Deceleration Time of early diastolic MV transmitral flow |
| E/A ratio | Ratio of early and late diastolic transmitral flow |
| MV-A | Late diastolic transmitral flow |
| MV-Adur | Duration of late diastolic transmitral flow |
| MV-E | Early diastolic transmitral flow |
| e' lateral | Early diastolic tissue velocity taken from the lateral region |
| e' mean | Mean early diastolic tissue velocity (mean of lateral and septal region) |
| e' septal | Early diastolic tissue velocity taken from the septal region |
| E/e' lateral | Ratio of early transmitral flow and early diastolic tissue velocity taken form the lateral region |
| E/e' septal | Ratio of early transmitral flow and early diastolic tissue velocity taken form the septal region |
| E/e' mean | Ratio of early transmitral flow and mean diastolic tissue velocity |
| a' lateral | Late diastolic tissue velocity taken from the lateral region |
| a' septal | Late diastolic tissue velocity taken from the septal region |
| s' lateral | Systolic tissue velocity taken from the lateral region |
| s' septal | Systolic tissue velocity taken from the septal region |
| LAESV A-L biplane | Left Atrial End Systolic Volume biplane calculation based on Area-Length method |
| LAESV MOD biplane | Left Atrial End Systolic Volume biplane calculation based on Method Of Discs |
| LAESVi MOD biplane | Left Atrial End Systolic Volume biplane calculation based on Method Of Discs indexed to BSA |
| LAESVi A-L biplane | Left Atrial End Systolic Volume biplane calculation based on Area-Length method indexed to BSA |
| LVCO MOD biplane | Left Ventricular Cardiac Output biplane calculation based on Method Of Discs |
| LVEDV MOD biplane | Left Ventricular End Diastolic Volume biplane calculation based on Method Of Discs |
| LVEDVi MOD biplane | Left Ventricular End Diastolic Volume biplane calculation based on Method Of Discs indexed to BSA |
| LVEF MOD biplane | Left Ventricular Ejection Fraction biplane based on Method Of Discs |
| LVESV MOD biplane | Left Ventricular End Systolic Volume biplane calculation based on Method Of Discs |
| LVESVi MOD biplane | Left Ventricular End Systolic Volume biplane calculation based on Method Of Discs indexed to BSA |
| LVSV MOD biplane | Left Ventricular Stroke Volume biplane calculation based on Method Of Disks |
| AoV Vmax | Aortic Valve maximum Velocity |
| AoV Vmean | Aortic Valve mean Velocity |
| AoV Pmax | Aortic Valve maximum Pressure gradient |
| LVOT Vmax | Left Ventricular Outflow Tract maximum Velocity |
| LVOT Vmean | Left Ventricular Outflow Tract mean Velocity |

-continued

| Measurement Name | Measurement Description |
| --- | --- |
| IVSd | Inter Ventricular Septal thickness measured end diastolic |
| LV mass | Left Ventricular mass |
| LVIDd | Left Ventricular internal Diameter measured at end diastole |
| LVIDd index | Left Ventricular internal Diameter measured at end diastole indexed to BSA |
| LVIDs | Left Ventricular internal Diameter measured at end systole |
| LVIDs index | Left Ventricular internal Diameter measured at end systole indexed to BSA |
| LVMi | Left Ventricular Mass indexed to BSA |
| LVOT | Left Ventricular Outflow Tract diameter |
| LVPWd | Left Ventricular Posterior Wall thickness measured end diastolic |
| RWT | Relative Wall Thickness |
| LA area A2C | Left Atrial Area measured in A2C |
| LAESV A-L A2C | Left Atrial End Systolic Volume in A2C calculation based on Area-Length method |
| LVAd A2C | Left Ventricular Area measured at end diastole in A2C |
| LVAs A2C | Left Ventricular Area measured at end systole in A2C |
| LVAs A4C | Left Ventricular Area measured at end systole in A4C |
| PASP | Pulmonary Artery Systolic Pressure |
| RAL | Right Atrial End Systolic Length |
| RAW | Right Atrial End Systolic Width |
| RAESV MOD A4C | Right Atrial end systolic Volume in A4C calculation based on Method Of Discs |
| RAESV A-L A4C | Right Atrial end systolic Volume in A4C calculation based on Area-Length method |
| RAESVi MOD A4C | Right Atrial end systolic Volume in A4C calculation based on Method Of Discs indexed to BSA |
| RA area | Right Atrial area |
| RVIDd | Right Ventricular End Diastolic Internal Diameter |
| RV area (d) | Right Ventricular Area (measured at end-diastole) |
| RV area (s) | Right Ventricular Area (measured at end systole) |
| LVOT Pmax | Left Ventricular Outflow Tract max pressure gradient |
| LVOT Pmean | Left Ventricular Outflow Tract mean pressure gradient |
| LVSV (Doppler) | Left Ventricular Stroke Volume based on Doppler |
| LVOT VTI | Left Ventricular Outflow Tract Velocity Time Integral |
| LVCO (Doppler) | Left Ventricular Cardiac Output (based on Doppler) |
| LVCOi (Doppler) | Left Ventricular Cardiac Output (based on Doppler) indexed to Body Surface Area |
| LVSVi (Doppler) | Left Ventricular Stroke Volume (based on Doppler) indexed to Body Surface Area |
| TR Vmax | Tricuspid Regurgitation maximum velocity |
| CSA LVOT | Crossectional Area of the LVOT |
| Sinotub J | Sinotubular junction diameter |
| Sinus valsalva | Sinus valsalva diameter |
| Asc. Ao | Ascending Aorta diameter |
| Asc. Ao index | Ascending Aorta diameter index |
| Sinus valsalva index | Sinus valsalva diameter indexed to BSA |
| IVC max | Inferior Vena Cava maximum diameter |
| IVC min | Inferior Vena Cava minimum diameter |
| IVC Collaps | Inferior Vena Cava collaps |
| RVIDd mid | Right Ventricular Internal Diameter at mid level (measured end diastole) |
| RVOT prox | Right Ventricular Outflow Tract proximal diameter |
| RVOT dist | Right Ventricular Outflow Tract distal diameter |
| RV FAC | Right Ventricular Fractional Area Change |
| TE I index | |
| RVAWT | Right Ventricular Anterior Wall Thickness |
| TrV-E | Tricuspid valve E wave |
| TrV-A | Tricuspid valve A wave |
| TrV E/A | Tricuspid valve E/A ratio |
| TrV DecT | Tricuspid valve deceleration time |
| MV Vmax | Mitral valve maximum velocity |
| MV Vmean | Mitral valve mean velocity |
| MV VTI | Mitral valve velocity time intergal |
| MV PHT | Mitral valve pressure half time |
| MVA (by PHT) | Mitral valve area (by pressure half time) |
| RV e' | Early diastolic tissue velocity taken from the right ventricular free wall region |
| RV a' | Late diastolic tissue velocity taken from the right ventricular free wall region |
| RV s' | Systolic tissue velocity taken from the right ventricular free wall region |
| RVCO | Right Ventricular Cardiac Output |

-continued

| Measurement Name | Measurement Description |
| --- | --- |
| ULS | Unidimensional Longitudinal Strain |
| Ao-arch | Aortic arch diameter |
| Descending Ao | Descending Aortic diameter |
| Ao-arch index | Aortic arch diameter indexed to BSA |
| Descending Ao index | Descending Aortic diameter indexed to BSA |
| LA GLS (reservoir) (A4C) | Left Atrial strain during systole measured in A4C |
| LA GLS (conduit) (A4C) | Left Atrial strain during early diastole measured in A4C |
| LA GLS (booster) (A4C) | Left Atrial strain during pre atrial contraction measured in A4C |
| LA GLS (reservoir) (A2C) | Left Atrial strain during systole measured in A2C |
| LA GLS (conduit) (A2C) | Left Atrial strain during early diastole measured in A2C |
| LA GLS (booster) (A2C) | Left Atrial strain during pre atrial contraction measured in A2C |
| LA GLS (reservoir) | Left Atrial strain during systole |
| LA GLS (conduit) | Left Atrial strain during early diastole |
| LA GLS (booster) | Left Atrial strain during pre atrial contraction |
| LVSr-e (A4C) | Left Ventricular strain rate during early diastole measured in A4C |
| LVSr-a (A4C) | Left Ventricular strain rate during late diastole measured in A4C |
| LVSr-s (A4C) | Left Ventricular strain rate during systole measured in A4C |
| LVSr-e (A2C) | Left Ventricular strain rate during early diastole measured in A2C |
| LVSr-a (A2C) | Left Ventricular strain rate during late diastole measured in A2C |
| LVSr-s (A2C) | Left Ventricular strain rate during systole measured in A2C |
| LVSr-e | Left Ventricular strain rate during early diastole |
| LVSr-a | Left Ventricular strain rate during late diastole |
| LVSr-s | Left Ventricular strain rate during systole |
| LASr-e (A4C) | Left Atrial strain rate during early diastole |
| LASr-a (A4C) | Left Atrial strain rate during late diastole |
| LASr-s (A4C) | Left Atrial strain rate during systole |
| LASr-e (A2C) | Left Atrial strain rate during early diastole |
| LASr-a (A2C) | Left Atrial strain rate during late diastole |
| LASr-s (A2C) | Left Atrial strain rate during systole |
| LASr-e | Left Atrial strain rate during early diastole |
| LASr-a | Left Atrial strain rate during late diastole |
| LASr-s | Left Atrial strain rate during systole |
| AV-S (A4C) | Atrio Ventricular strain measured in A4C |
| AV-S (A2C) | Atrio Ventricular strain measured in A2C |
| AV-S | Atrio Ventricular strain |
| Sr-Sav (A4C) | Atrio Ventricular strain rate during systole measured in A4C |
| Sr-Eav (A4C) | Atrio Ventricular strain rate during early diastole measured in A4C |
| Sr-Aav (A4C) | Atrio Ventricular strain rate during late diastole measured in A4C |
| Sr-Sav (A2C) | Atrio Ventricular strain rate during systole measured in A2C |
| Sr-Eav(A2C) | Atrio Ventricular strain rate during early diastole measured in A2C |
| Sr-Aav (A2C) | Atrio Ventricular strain rate during late diastole measured in A2C |
| Sr-Sav | Atrio Ventricular strain rate during systole |
| Sr-Eav | Atrio Ventricular strain rate during early diastole |
| Sr-Aav | Atrio Ventricular strain rate during late diastole |
| LVVr-e (A4C) | Left Ventricular volume rate during early diastole measured in A4C |
| LVVr-a (A4C) | Left Ventricular volume rate during late diastole measured in A4C |
| LVVr-s (A4C) | Left Ventricular volumerate during systole measured in A4C |
| LVVr-e (A2C) | Left Ventricular volume rate during early diastole measured in A2C |
| LVVr-a (A2C) | Left Ventricular volume rate during late diastole measured in A2C |
| LVVr-s (A2C) A2C | Left Ventricular volumerate during systole measured in |
| LVVr-e | Left Ventricular volume rate during early diastole |
| LVVr-a | Left Ventricular volume rate during late diastole |
| LVVr-s | Left Ventricular volumerate during systole |
| LAVr-e (A4C) | Left Atrial volume rate during early diastole measured in A4C |
| LAVr-a (A4C) | Left Atrial volume rate during late diastole measured in A4C |

-continued

| Measurement Name | Measurement Description |
| --- | --- |
| LAVr-s (A4C) | Left Atrial volumerate during systole measured in A4C |
| LAVr-e (A2C) | Left Atrial volume rate during early diastole measured in A2C |
| LAVr-a (A2C) | Left Atrial volume rate during late diastole measured in A2C |
| LAVr-s (A2C) | Left Atrial volumerate during systole measured in A2C |
| LAVr-e | Left Atrial volume rate during early diastole |
| LAVr-a | Left Atrial volume rate during late diastole |
| LAVr-s | Left Atrial volumerate during systole |
| TLVd | Total Left heart volume end-diastolic |
| TLVs | Total Left heart volume end-systolic |
| TLVd (A4C) | Total Left heart volume end-diastolic measured in A4C |
| TLVs (A4C) | Total Left heart volume end-systolic measured in A4C |
| TLVd (A2C) | Total Left heart volume end-diastolic measured in A2C |
| TLVs (A2C) | Total Left heart volume end-systolic measured in A2C |
| Ar | Pulmonary vein Atrial reversal flow |
| Ardur | Pulmonary vein Atrial reversal flow duration |
| D | Pulmonary vein diastolic flow velocity |
| S | Pulmonary vein systolic flow velocity |
| S/D ratio | Ratio of Pulmonary vein systolic- and diastolic flow Vel. |
| RV GLS | Right Ventricular Global Longitudinal Strain (mean) |
| RV GLS (A4C) | Right Ventricular Global Longitudinal Strain measured in A4C |
| RV GLS (A2C) | Right Ventricular Global Longitudinal Strain measured in A2C |
| RV GLS (A3C) | Right Ventricular Global Longitudinal Strain measured in A3C |
| LA GLS | Left Atrial Global Longitudinal Strain (mean) |
| LA GLS (A4C) | Left Atrial Global Longitudinal Strain measured in A4C |
| LA GLS (A2C) | Left Atrial Global Longitudinal Strain measured in A2C |
| LA GLS (A3C) | Left Atrial Global Longitudinal Strain measured in A3C |
| RA GLS | Right Atrial Global Longitudinal Strain (mean) |
| RA GLS (A4C) | Right Atrial Global Longitudinal Strain measured in A4C |
| RA GLS (A2C) | Right Atrial Global Longitudinal Strain measured in A2C |
| RA GLS (A3C) | Right Atrial Global Longitudinal Strain measured in A3C |
| PV Vmax | Pulmonary Valve maximum Velocity |
| PV Vmean | Pulmonary Valve mean Velocity |
| PV Pmax | Pulmonary Valve maximum Pressure gradient |
| PV Pmean | Pulmonary Valve mean Pressure gradient |
| PV VTI | Pulmonary Valve Velocity Time Integral |
| MV-Adur-Ardur | Difference between late diastolic transmitral flow and pulmonary vein atrial reversal flow duration |
| APC | Arteria pulmonalis communis |
| LV eccentricity index | LV eccentricity index |
| Mean % WT A2C | Mean percentual Wall Thickening of 6 segments in A2C |
| AA-% WT | Percentile wall thickening of apical anterior segment |
| AA-WTd | Wall thickness of apical anterior segment in diastole |
| AA-WTs | Wall thickness of apical anterior segment in systole |
| AI-% WT | Percentile wall thickening of apical inferior segment |
| AI-WTd | Wall thickness of apical inferior segment in diastole |
| AI-WTs | Wall thickness of apical inferior segment in systole |
| BA-% WT | Percentile wall thickening of basal anterior segment |
| BA-WTd | Wall thickness of basal anterior segment in diastole |
| BA-WTs | Wall thickness of basal anterior segment in systole |
| BI-% WT | Percentile wall thickening of basal interior segment |
| BI-WTd | Wall thickness of basal interior segment in diastole |
| BI-WTs | Wall thickness of basal interior segment in systole |
| MA-% WT | Percentile wall thickening of mid anterior segment |
| MA-WTd | Wall thickness of mid anterior segment in diastole |
| MA-WTs | Wall thickness of mid anterior segment in systole |
| MI-% WT | Percentile wall thickening of mid inferior segment |
| MI-WTd | Wall thickness of mid inferior segment in diastole |
| MI-WTs | Wall thickness of mid inferior segment in systole |
| Pericardial effusion | Pericardial effusion |
| Mean % WT A3C | Mean percentual Wall Thickening of 6 segments in A3C |
| AAS-% WT | Percentile wall thickening of apical antero-septal segment |
| AAS-WTd | Wall thickness of apical antero-septal segment in diastole |
| AAS-WTs | Wall thickness of apical antero-septal segment in systole |
| AP-% WT | Percentile wall thickening of apical posterior segment |
| AP-WTd | Wall thickness of apical posterior segment in diastole |

-continued

| Measurement Name | Measurement Description |
| --- | --- |
| AP-WTs | Wall thickness of apical posterior segment in systole |
| BAS-% WT | Percentile wall thickening of basal antero-septal segment |
| BAS-WTd | Wall thickness of basal antero-septal segment in diastole |
| BAS-WTs | Wall thickness of basal antero-septal segment in systole |
| BP-% WT | Percentile wall thickening of basal posterior segment |
| BP-WTd | Wall thickness of basal posterior segment in diastole |
| BP-WTs | Wall thickness of basal posterior segment in systole |
| MAS-% WT | Percentile wall thickening of mid antero-septal segment |
| MAS-WTd | Wall thickness of mid antero-septal segment in diastole |
| MAS-WTs | Wall thickness of mid antero-septal segment in systole |
| MP-% WT | Percentile wall thickening of mid posterior segment |
| MP-WTd | Wall thickness of mid posterior segment in diastole |
| MP-WTs | Wall thickness of mid posterior segment in systole |
| Mean % WT A4C | Mean percentual Wall Thickening of 6 segments in A4C |
| AL-% WT | Percentile wall thickening of apical lateral segment |
| AL-WTd | Wall thickness of apical lateral segment in diastole |
| AL-WTs | Wall thickness of apical lateral segment in systole |
| AS-% WT | Percentile wall thickening of apical septal segment |
| AS-WTd | Wall thickness of apical septal segment in diastole |
| AS-WTs | Wall thickness of apical septal segment in systole |
| BL-% WT | Percentile wall thickening of basal lateral segment |
| BL-WTd | Wall thickness of basal lateral segment in diastole |
| BL-WTs | Wall thickness of basal lateral segment in systole |
| BS-% WT | Percentile wall thickening of basal septal segment |
| BS-WTd | Wall thickness of basal septal segment in diastole |
| BS-WTs | Wall thickness of basal septal segment in systole |
| ML-% WT | Percentile wall thickening of mid lateral segment |
| ML-WTd | Wall thickness of mid lateral segment in diastole |
| ML-WTs | Wall thickness of mid lateral segment in systole |
| MS-% WT | Percentile wall thickening of mid septal segment |
| MS-WTd | Wall thickness of mid septal segment in diastole |
| MS-WTs | Wall thickness of mid septal segment in systole |
| Global % WT | Global percentual Wall Thickening of the Left Ventricle |
| AoV Vmean | Aortic Valve mean Velocity |
| AoV Pmean | Aortic Valve mean Pressure gradient |
| AoV VTI | Aortic Valve Velocity Time Integral |
| AVA Vmax | Aortic Valve Area (measured by max Vel.) |
| AVA VTI | Aortic valve Area (measured by Velocity Time Integral) |
| AVAi Vmax | Aortic Valve Area (measured by maximum Velocity) indexed to Body Surface Area |
| AVAi VTI | Aortic valve Area (measured by Velocity Time Integral) indexed to Body Surface Area |
| ivrt | IsoVolumic Relaxation Time |
| LV GLS (A4C) | Left Ventricular Global Longitudinal Strain measured in A4C |
| LV GLS (A2C) | Left Ventricular Global Longitudinal Strain measured in A2C |
| LV GLS (A3C) | Left Ventricular Global Longitudinal Strain measured in A3C |
| LV GLS | Left Ventricular Global Longitudinal Strain (mean) |

Referring again to FIG. 4A, in one embodiment, the echo workflow engine 12 maintains measurement confidence scores corresponding to the measured left/right ventricles, left/right atriums, LVOTs, pericardiums and measured velocities. The echo workflow engine 12 filters out echo images having measurement confidence scores that fail to meet a threshold, i.e., low measurement confidence scores (block 442).

Measurement of cardiac features continues with calculating longitudinal strain graphs using the annotations generated by the CNNs (block 444). Thereafter, a fifth CNN is optionally used to detect pericardial effusion 446.

FIG. 11 is a diagram graphically illustrating measurements of global longitudinal strain that were automatically generated from the annotations of cardiac chambers in 2D images.

Referring again to FIG. 4A, for all remaining non-filtered out data, the echo workflow engine 12 selects as best measurement data the measurements associated with cardiac chambers with the largest volumes, and saves with the best measurement data, image location, classification, annotation and other measurement data associated with the best measurements (block 447).

FIG. 12A is a diagram graphically illustrating an example set of best measurement data 1200 based on largest volume cardiac chambers and the saving of the best measurement data 1200 to a repository, such as database 16 of FIG. 1.

Referring again to FIG. 4A, the echo workflow engine 12 then generates conclusions by inputting the best measurement data 1200 to a set of rules based on international measurement guidelines to generate conclusions for medical decisions support (block 448).

Figure 12B:
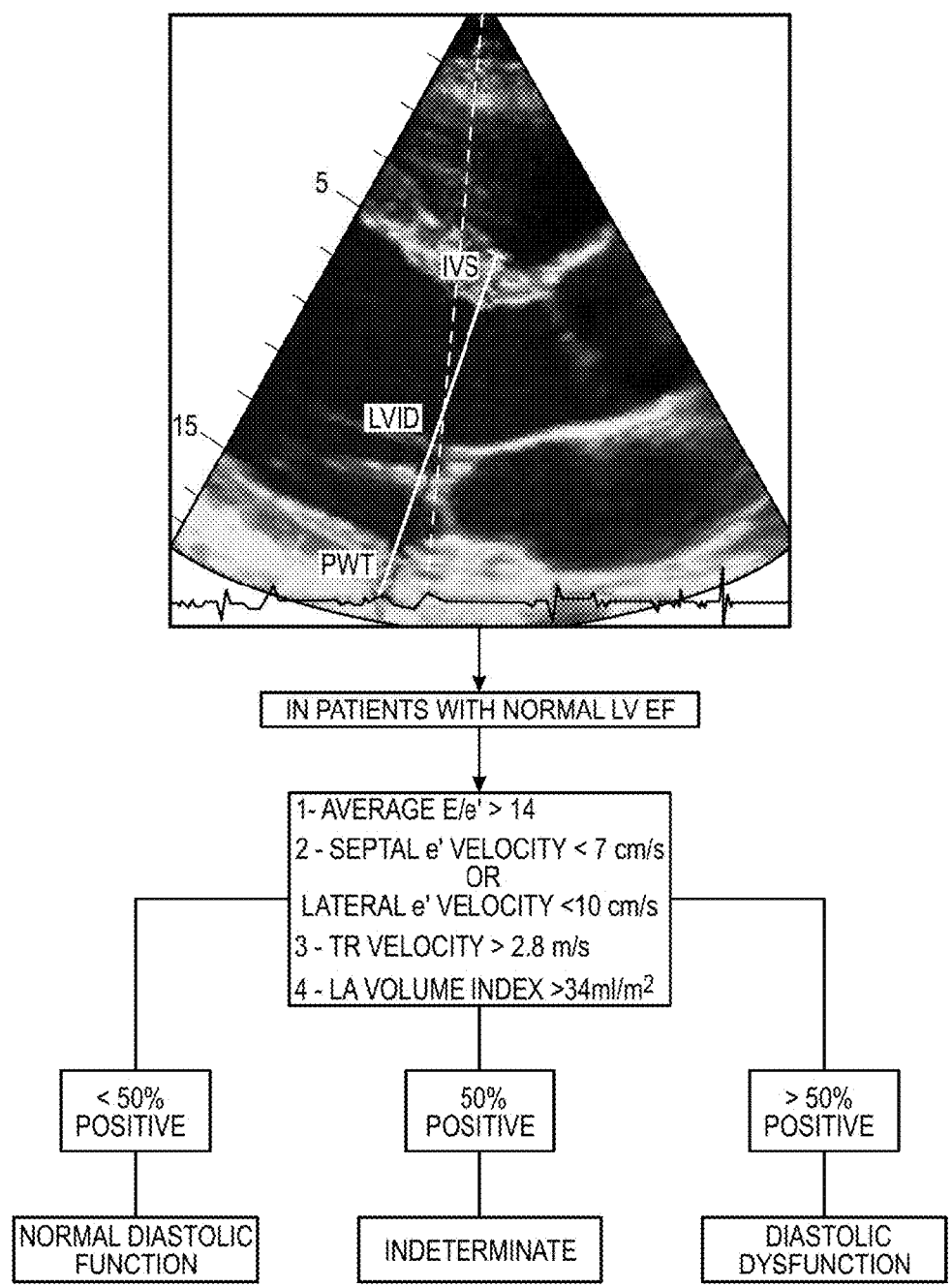
FIG. 12B is a diagram graphically illustrating the input of automatically derived measurements from a patient with normal LV EF measurements into a set of rules to determine a conclusion that the patient has normal diastolic function, diastolic dysfunction, or indeterminate.

FIG. 12B is a diagram graphically illustrating the input of normal LV EF measurements into a set of rules to determine a conclusion that the patient has normal diastolic function, diastolic dysfunction, or indeterminate.

Referring again to FIG. 4A, after the conclusions are generated, a report is generated and output (FIG. 3 block 314), which may comprise blocks 450-456. Report generation may begin by the echo workflow engine 12 outputting the best measurement data 1200 to a JSON file for flexibility of export to other applications (block 450).

Figure 13:
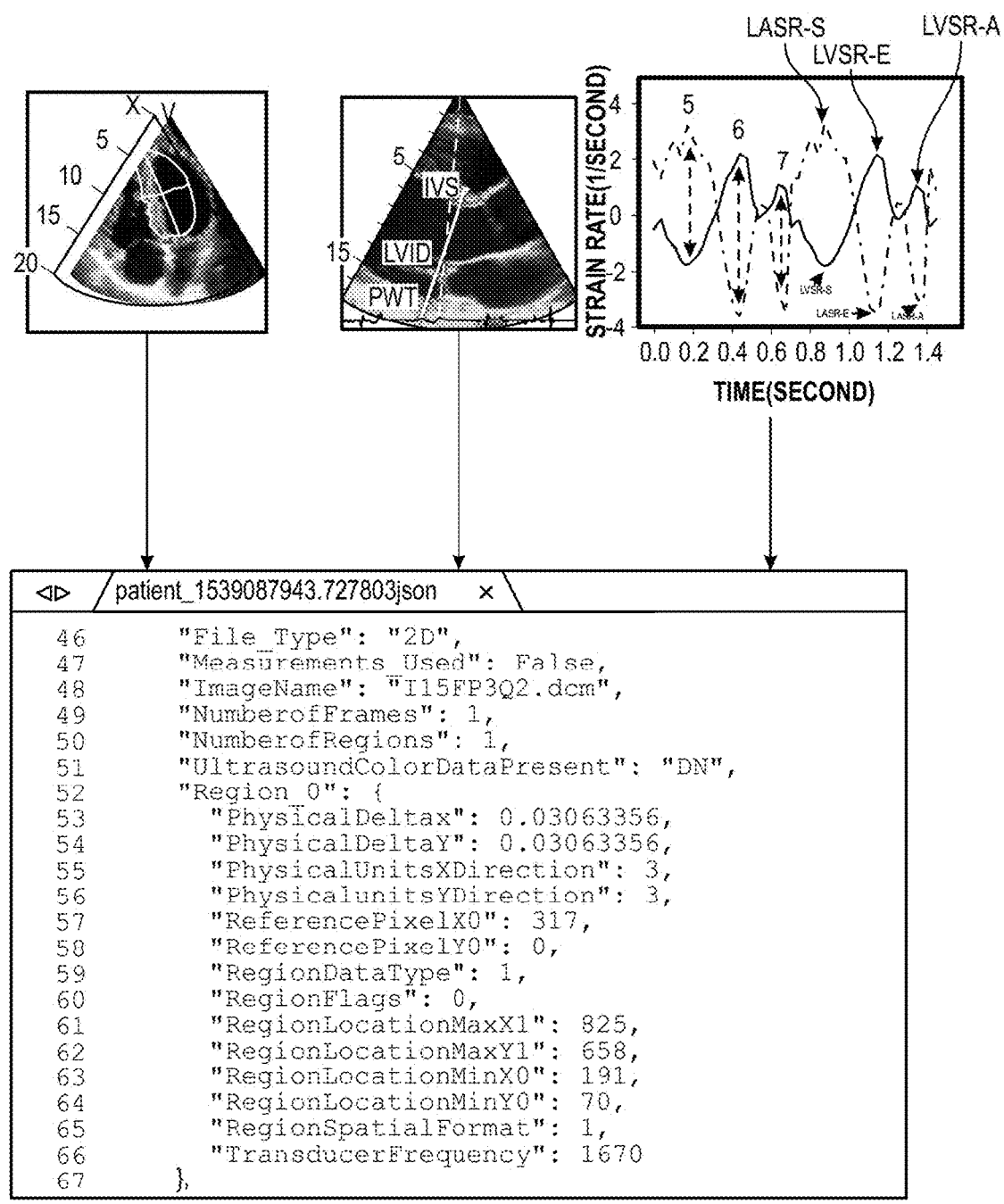
FIG. 13 is a diagram graphically illustrating the output of classification, annotation and measurement data to an example JSON file.

FIG. 13 is a diagram graphically illustrating the output of classification, annotation and measurement data to an example JSON file.

Referring again to FIG. 4A, a lightweight browser-based user interface (UI) displayed showing a report that visualizes the best measurement data 1200 from the JSON file and that is editable by a user (e.g., doctor/technician) for human verification (block 452). As is well known, a lightweight web browser is a web browser that is optimize to reduce consumption of system resources, particularly to minimize memory footprint, and by sacrificing some of the features of a mainstream web browser. In one embodiment, any edits made to the data are stored in the database 16 and displayed in the UI.

In order to make clinically relevant suggestion to the user, measurements associated with the best measurement data 1200 are automatically compared to current International guideline values and any out of range values are highlighted for the user (block 454).

FIG. 14 is a diagram illustrating a portion of an example report showing highlighting values that are outside the range of International guidelines.

Referring again to FIG. 4A, the user is provided with an option of generating a printable report showing an automated summary of Main Findings (i.e., a conclusion reached after examination) and underlining measurements of the patient's health (block 456).

FIG. 15 is a diagram illustrating a portion of an example report of Main Findings that may be printed and/or displayed by the user.

In one embodiment, the automated workflow of the echo workflow engine 12 may end at block 456. However, in further aspects of the disclosed embodiments, the process may continue with advance functions, as described below.

Figure 4B:
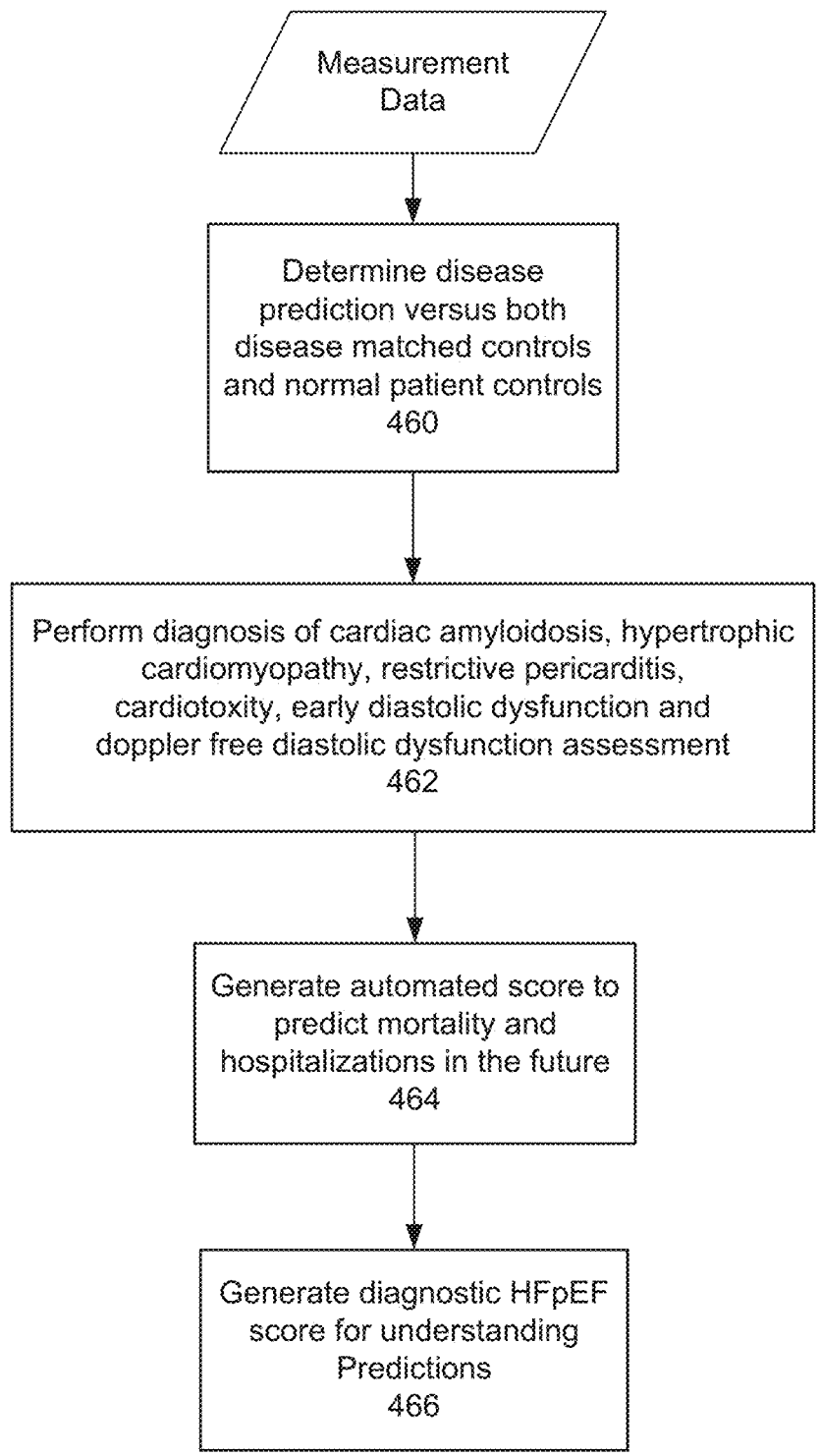
FIG. 4B is a flow diagram illustrating advanced functions of the echo workflow engine.

FIG. 4B is a flow diagram illustrating advanced functions of the echo workflow engine. According to this embodiment, the echo workflow engine 12, takes as inputs values of specific measurements that were automatically derived using machine learning (see block 310), and analyzes the specific measurements to determine disease diagnosis/prediction/prognosis versus both disease and matched controls and normal patient controls (block 460). In one embodiment, the echo workflow engine 12 may use the disease predictions to perform diagnosis of any combination of: cardiac amyloidosis, hypertrophic cardiomyopathy, restrictive pericarditis, cardiotoxity, early diastolic dysfunction and Doppler free diastolic dysfunction assessment (block 462). A prognosis in the form of an automated score may then be generated to predict mortality and hospitalizations in the future (block 464).

Echocardiography is key for the diagnosis of heart failure with preserved ejection fraction (HFpEF). However, existing guidelines are mixed in their recommendations for echocardiogram criteria and none of the available guidelines have been validated against gold-standard invasive hemodynamic measurements in HFpEF.

According to one embodiment, the echo workflow engine 12 further generates a diagnostic score for understanding predictions (block 466). Using machine learning, the echo workflow engine 12 validates the diagnostic score against invasively measured pulmonary capillary wedge pressure (PCWP), and determines the prognostic utility of the score in a large HFpEF cohort.

In one embodiment, the echo workflow engine 12, takes as the inputs values of specific measurements that were automatically derived using machine learning workflow, and analyzes the input values using an HFpEF algorithm to compute the HFpEF diagnostic score.

Recognizing that hypertensive heart disease is the most common precursor to HFpEF and has overlapping echocardiogram characteristics with HFpEF, echocardiogram features of 233 patients with HFpEF (LVEF≥50%) was compared to 273 hypertensive controls with normal ejection fraction but no heart failure. An agnostic model was developed using penalized logistic regression model and Classification and Regression Tree (CART) analysis. The association of the derived echocardiogram score with invasively measured PCWP was investigated in a separate cohort of 96 patients. The association of the score with the combined clinical outcomes of cardiovascular mortality of HF hospitalization was investigated in 653 patients with HFpEF from the Americas echocardiogram sub study of the TOPCAT trial.

According to one embodiment, left ventricular ejection fraction (LVEF<60%), peak TR velocity (>2.3 m/s), relative wall thickness (RWT>0.39 mm), interventricular septal thickness (>12.2 mm) and E wave (>1 m/s) are selected as the most parsimonious combination of variables to identify HFpEF from hypertensive controls. A weighted score (range 0-9) based on these 5 echocardiogram variables had a combined area under the curve of 0.9 for identifying HFpEF from hypertensive controls.

Figure 16A:
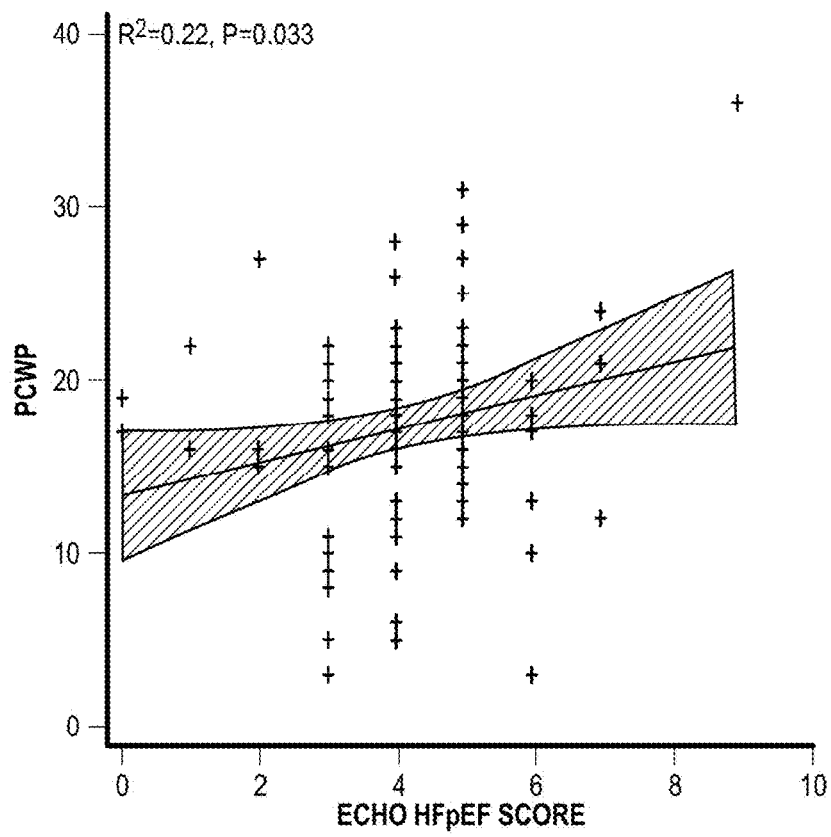
FIG. 16A is a diagram showing a graph A plotting PCWP and HFpEF scores.
Figure 16B:
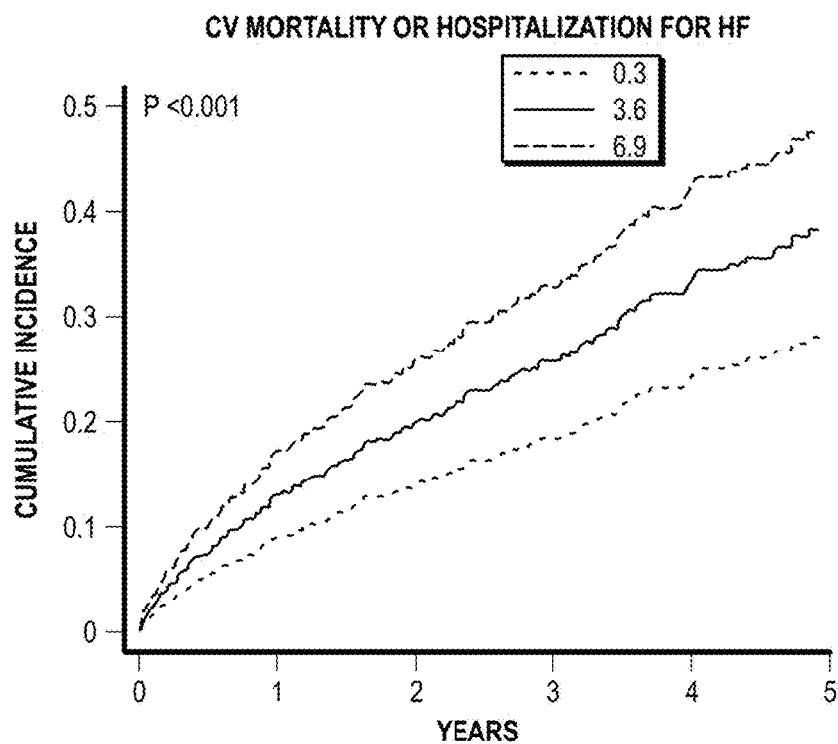
FIG. 16B is a diagram showing a graph B plotting CV mortality or hospitalization for HF.

FIGS. 16A and 16B are diagrams showing a graph A plotting PCWP and HFpEF scores, and a graph B plotting CV mortality or hospitalization for HF, respectively. Graph A shows that in the independent cohort, the HFpEF score was significantly associated with PCWP in patients with HFpEF ($R^2$=0.22, P=0.034). Graph B shows that a one-point increase was associated with a 12% increase in risk (hazard ratio [HR] 1.12; 95% Cl 1.02-1.23, P=0.015) for the combined outcome after multivariable correction.

According to the disclosed embodiments, the echocardiographic score can distinguish HFpEF from hypertensive controls and is associated with objective measurements of severity and outcomes in HFpEF.

Neural Network Training

Figure 17:
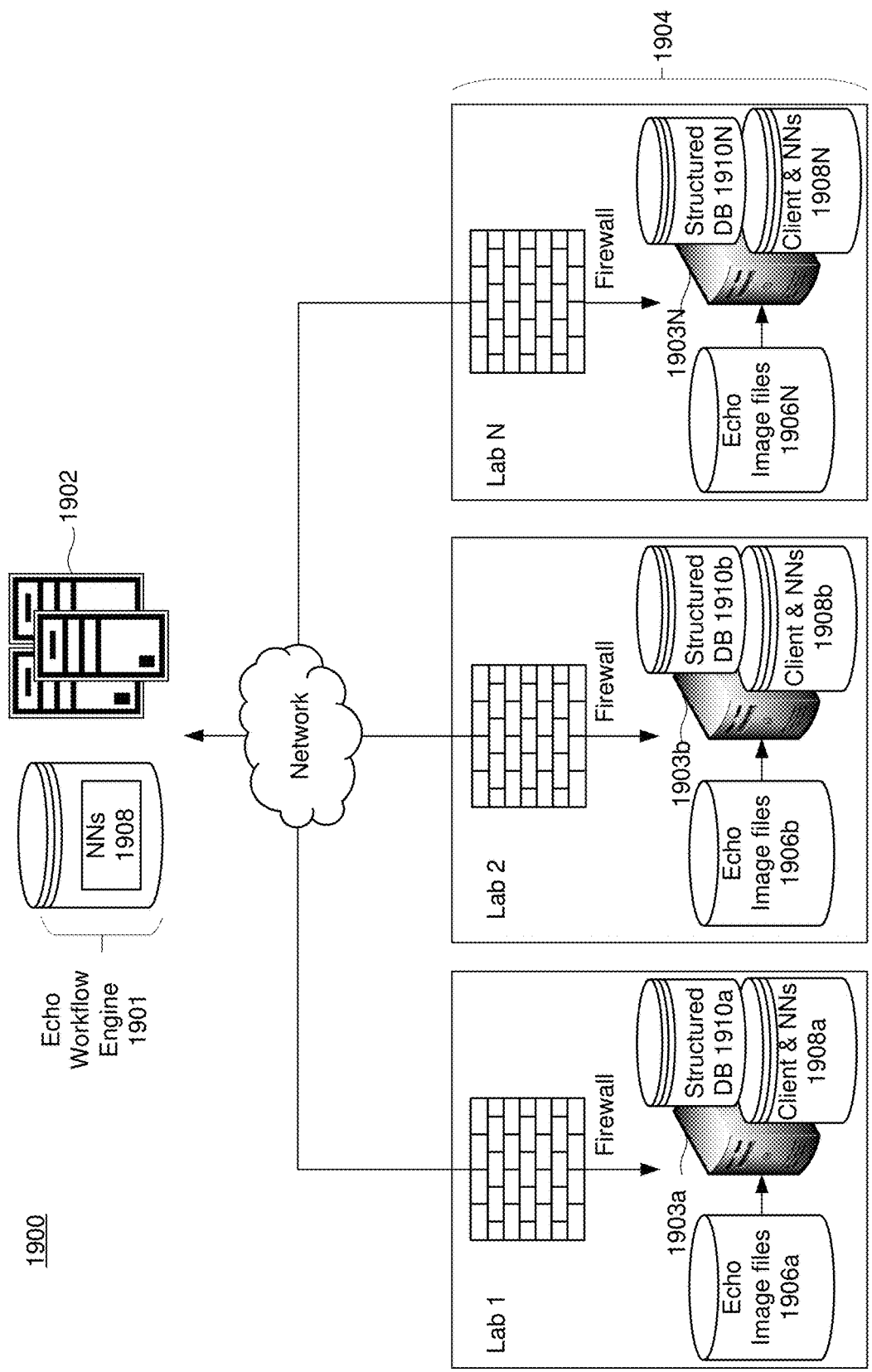
FIG. 17 is a diagram illustrating a federated training platform associated with the automated clinical workflow system.

According to a further aspect of the disclosed embodiments, the eko workflow engine 12 incorporates a federated training platform for effectively training the assortment of the neural networks employed by the machine learning layer 200 (FIG. 2), as shown in FIG. 17.

FIG. 17 is a diagram illustrating a federated training platform associated with the automated clinical workflow system. According to one embodiment, the federated training platform 1900 comprises the eko workflow engine 1901 executing on one or more servers 1902 in the cloud. As described above, the eko workflow engine 1901 comprises multiple neural networks (NNs) 1908, which may include some combination of GANs and CNNs, for example. The servers 1902 and eko workflow engine 1901 are in network communication with remote computers 1903a, 1903b, 1903n (collectively computers 1903) located on premises at respective laboratories 1904 (e.g., lab 1, lab2 . . . , lab N).

Each of the laboratories 1904 maintains image file archives comprising, for example, echocardiogram image files 1906a, 1906b . . . , 1906N (collectively echo image files 1906) of patient cohorts. For example, the laboratories 1904 may comprise a hospital or clinical lab environment where Echocardiography is performed as a diagnostic aid in cardiology for the morphological and functional assessment of the heart. When performing echocardiography and taking manual measurements, doctors typically select a small subset of the available videos from the echo image files 1906, and may only measure about two of the frames in those videos, which typically may have 70-100 image frames each.

To increase the accuracy of the neural networks comprising the eko workflow engine, it would be desirable to make use of the each lab's echo image files 1906 as training data for machine learning. However, some or all of the labs 1904 may treat the image file archives as proprietary (graphically illustrated by the firewall), and thus do not allow their echo image files 1906 to leave the premises, which means the echo image files 1906 are unavailable as a source of training data.

According to another aspect of the disclosed embodiments, the federated training platform 1900 unlocks the proprietary echo image files 1906 of the separate laboratories 1904. This is done by downloading and installing lightweight clients and a set of NNs 1908a, 1908b, 1908c on computers 1903a, 1903b, 1903c (collectively computers 1903) local to the respective labs 1904. More specifically, lightweight client executing on computer 1903a of a first lab (Lab 1) accesses the first lab's echo image files 1906a and uses those echo image files 1906a to train the NNs 1908a and upload a first trained set of NNs back to the server 1902 after training. The first set of trained NNs 1908 are then trained at a second lab (e.g., lab 2) by downloading the lightweight clients and NNs 1908b the computer 1903b located at the second lab 2. The lightweight client executing on the computer 1903b of the second lab can then access the second lab's echo image files 1906b and use those echo image files 1906b to continue to continue to train the NNs 1908b and to upload a second trained of NNs set back to the server 1902. This process may continue until the NN's complete training at the last lab N by the lightweight client executing on the computer 14N of the last lab N to access lab N's echo image files 1906N to train the NNs and to upload a final trained set of neural networks to the server 1902. Once uploaded to the server 1902 the final train set of neural networks are then used in analysis mode to automatically recognize and analyze echo images in the patient studies of the respective labs 1904.

The federated training platform 1900 results in a highly trained set of NNs 1908 that produce measurements and predictions with a higher degree of accuracy. Another benefit is that federated training platform 1900 unlocks and extracts value from the existing stores of echo data. The echo image files 1906 from the laboratories 1904 previously represented vast numbers of echoes from past patient studies and clinical trials that sat unused and unavailable for machine learning purposes because the images are unstructured, views are un-labelled, and most of the images were ignored. Through the federated training platform 1900, these unused and unavailable echo images are now processed by the lightweight client of the eko workflow engine to create labelled echo images that are stored in structured image databases 1910a, 1910b . . . , 190N, at each of the labs 1904, which is a necessary prerequisite for any machine learning training or machine learning experiments performed on the images. In one embodiment, the structured image databases remain located on premises at the individual labs 1904 to comply with the security requirements (of the labs 1904 and/or the eko workflow engine 1901).

Accordingly, the federated training platform 1900 provides access to structured echo image databases 1910 in multiple lab locations to allow distributed neural network training and validation of disease prediction across multiple patient cohorts without the either the original echo images files 1906 or the labelled echo image files in the structured database 1910 ever having to leave the premise of the labs 1904.

As stated above, the segmentation CNNs may be trained from hand-labeled real images or artificial images generated by general adversarial networks (GANs).

Figure 18:
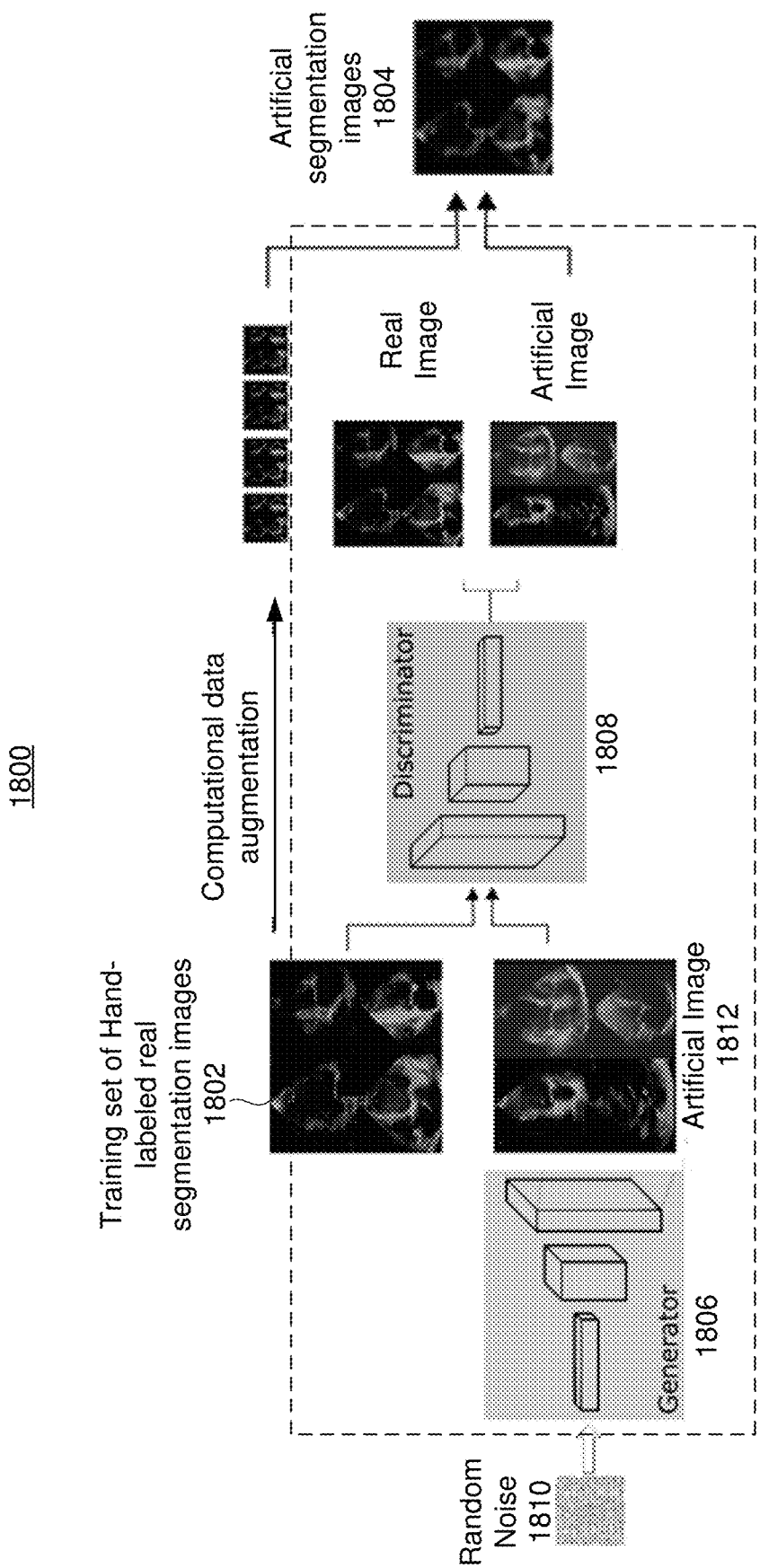
FIG. 18 is a diagram showing use of a GAN for creating image segmentation training data.

FIG. 18 is a diagram showing use of a GAN for creating image segmentation training data. A GAN is a class of neural networks that uses two neural networks, pitting one against the other adversarially in order to generate new, synthetic data that can pass for real data. For example, the GAN 1800 trained on a training set of hand-labeled segmentation images 1802 can generate artificial segmentation images similar to the training set.

The GAN 1800 comprises one neural network called a generator 1806 and another neural network called a discriminator 1808. The generator 1806 generates candidate artificial images, while the discriminator 1808 evaluates the candidate images to determine statistically which of the candidates belong to the training set and which do not. The discriminator 1808 is first trained based on samples from the training set 1802 until the discriminator 1808 achieves acceptable accuracy.

The generator 1806 is an inverse convolutional network that receives as input a vector of random noise 1810 and upsamples the random noise 1810 into an artificial image 1812. This generated artificial image 1812 is input into the discriminator 1808 along with a stream of images taken from the training set 1802. The discriminator 1808 is a standard convolutional network that receives both the real and fake images and classifies/categorizes the artificial images 1812 using binomial classifier labeling, such "Real" or "Artificial". Optionally, the discriminator may return probabilities, a number between 0 and 1, where 1 may represent a prediction of authenticity and 0 representing artificial. The discriminator 1808 is in a feedback loop with the training set of images 1802, which is known, so that the discriminator 1808 becomes more skilled at identifying artificial images. The generator 1806 is in a feedback loop with the discriminator 1808 so that the generator 1806 produces better candidate images. Both the training set 1902 and the artificial images can be used as a final training set 1904.

Figure 19:
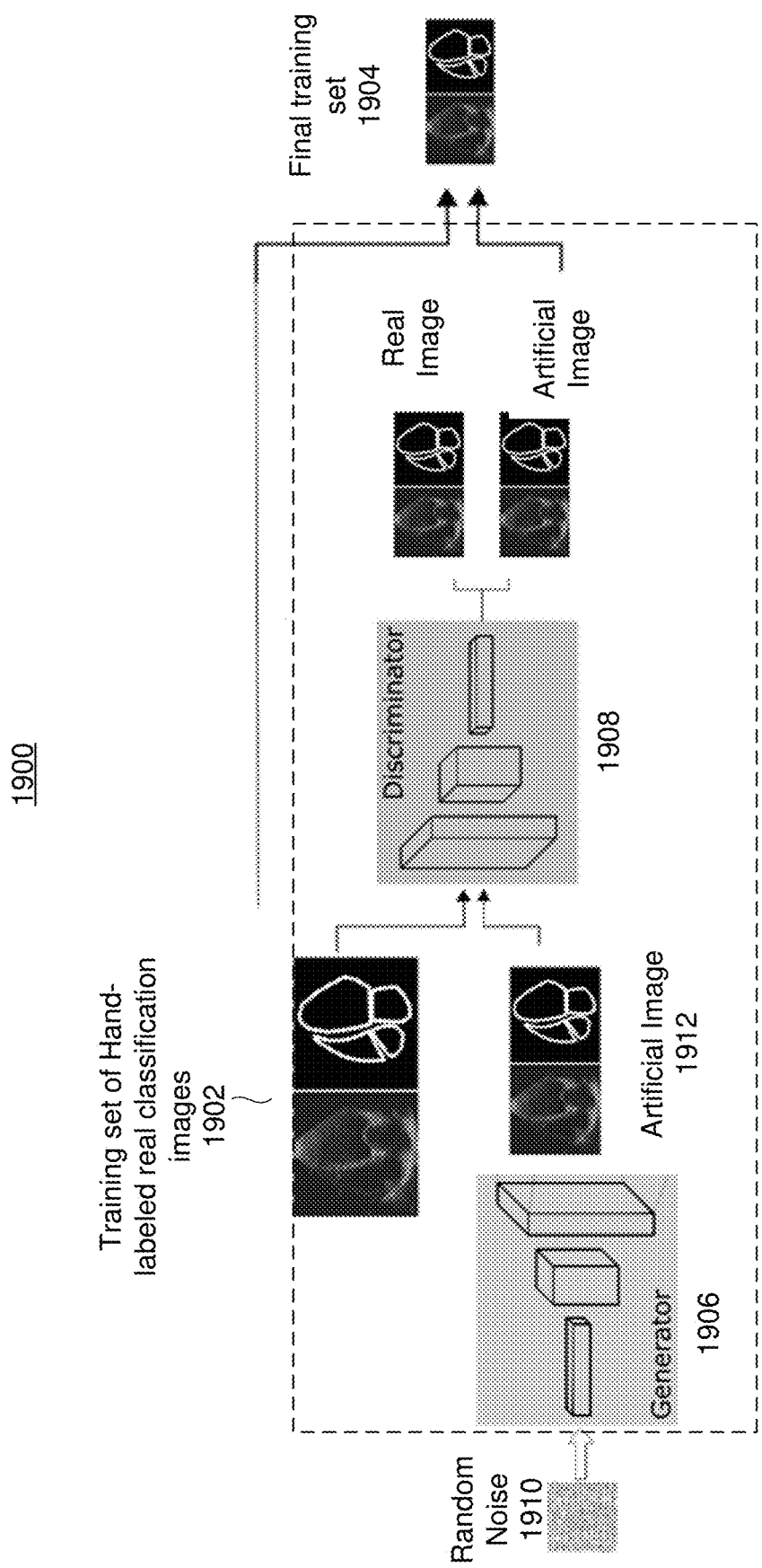
FIG. 19 is a diagram showing components of a GAN for creating view classification training data.

FIG. 19 is a diagram showing components of a GAN for creating view classification training data. GAN 1900 is similar to GAN 1800 in terms of structure and operation, except that the training 1902 set comprises hand-labeled real classification images and the final training set 1904 includes the training set 1902 and artificial classification images.

A method and system for training neural networks of a software-based automatic clinical workflow that recognizes and analyzes both 2D and Doppler modality Echocardiographic images for automated measurements and the diagnosis, prediction and prognosis of heart disease has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or an optical-ROM and is to be executed by a processor. Accordingly, many modifications may be made by one of ordinary skill in the art without departing from the spirit and scope of the appended claims.

We claim:

1. A computer-implemented method for training neural networks of an automated workflow performed by a software component executing on a server, the server in network communication with remote computers at respective laboratories, the respective laboratories maintaining image file archives comprising echocardiogram image files, the method comprising:
    downloading and installing a client and a set of neural networks to a first remote computer of a first laboratory, the client accessing the echocardiogram image files of the first laboratory to train the set of neural networks and to upload a first trained set of neural networks to the server;
    downloading and installing the client and the first trained set of neural networks to a second remote computer of a second laboratory, the client accessing the echocardiogram image files of the second laboratory to continue to train the first trained set of neural networks and to upload a second trained set of neural networks to the server; and
    continuing the process until the client and the second trained set of neural networks is downloaded and installed to a last remote computer of a last laboratory, the client accessing the echocardiogram image files of the last laboratory to continue to train the second trained set of neural networks and to upload a final trained set of neural networks to the server.

2. The method of claim 1, wherein the echocardiogram image file archives of one or more of the laboratories contain un-labelled echocardiogram images, the method further comprising: processing, by the client, the un-labeled echocardiogram images to create labelled echocardiogram images, and storing the labeled echocardiogram images in a structured database prior to training.

3. The method of claim 1, further comprising: storing the structured database locally at the one or more laboratories to comply with security requirements.

4. The method of claim 1, further comprising: storing the structured database remotely at the server.

5. The method of claim 1, further comprising: using both real echocardiogram images and artificial echocardiogram images as training data.

6. The method of claim 1, further comprising: using, by the software component executing on the server, the final trained set of neural networks in an analysis mode to automatically recognize and analyze the echocardiogram images in the patient studies of the respective labs.

7. The method of claim 6, wherein the software component automatically recognizes and analyzes echocardiogram images by:
    receiving, from a memory, one of the patient studies comprising a plurality of echocardiogram images;
    separating the plurality of echocardiogram (echo) images according to 2D images and Doppler modality images;
    classifying the 2D images by view type;
    extracting features of the Doppler modality images and using the extracted features to classify the Doppler modality images by region;
    segmenting each classified 2D view type to produce segmented 2D images;
    segmenting each classified the Doppler modality region to generate waveform traces to produce segmented Doppler modality images;
    using both the segmented 2D images and the segmented Doppler modality images to calculate for the patient study measurements of cardiac features for both left and right sides of the heart;
    generating conclusions by comparing the calculated measurements with International cardiac guidelines; and
    outputting a report highlighting ones of the calculated measurements that fall outside of the International cardiac guidelines.

8. The method of claim 7, further comprising: implementing the final trained set of neural networks in the analysis mode as:
    a first neural network to classify the 2D images by view type;
    a second set of neural networks to both extract features from Doppler modality images and to use the extracted features to classify the Doppler modality images by region;
    a third set of neural networks for each classified 2D view type in order to segment the cardiac chambers in the 2D images and produce segmented 2D images; and
    a fourth set of neural networks for each classified Doppler modality region in order to segment Doppler modality images to generate waveform traces.

9. The method of claim 8, further comprising: including in the final trained set of neural networks a set of one or more prediction CNNs for disease prediction and a set of one or more prognosis CNNs for disease prognosis.

10. The method of claim 8, further comprising: implementing the first neural network and the second set of neural networks as convolutional neural networks (CNNs).

11. The method of claim 10, further comprising: implementing the third set of neural networks as generative adversarial neural networks (GANs).

12. The method of claim 8, further comprising: using another set of the GANs at least in part to generate artificial segmentation training data and classification training data.

13. A system, comprising:
    a server comprising a memory and a processor coupled to the memory, the server in network communication with remote computers at respective laboratories, the respective laboratories maintaining image file archives comprising echocardiogram image files; and
    a workflow engine executed on the server that is configured to:
        download and install a client and a set of neural networks to a first remote computer of a first laboratory, the client accessing the echocardiogram image files of the first laboratory to train the set of neural networks and to upload a first trained set of neural networks to the server;
        download and install the client and the first trained set of neural networks to a second remote computer of a second laboratory, the client accessing the echocardiogram image files of the second laboratory to continue to train the first trained set of neural networks and to upload a second trained set of neural networks to the server; and continuing the process until the client and the second trained set of neural networks is downloaded and installed to a last remote computer of a last laboratory, the client accessing the echocardiogram image files of the last laboratory to continue to train the second trained set of neural networks and to upload a final trained set of neural networks to the server.

14. The system of claim 13, wherein the echocardiogram image file archives of one or more of the laboratories contain un-labelled echocardiogram images, the system further comprising: processing, by the client, the un-labeled echocardiogram images to create labelled echocardiogram images, and storing the labeled echocardiogram images in a structured database prior to training.

15. The system of claim 13, wherein the structured database is stored locally at the one or more laboratories to comply with security requirements.

16. The system of claim 13, wherein the structured database is stored remotely at the server.

17. The system of claim 13, wherein both real echocardiogram images and artificial echocardiogram images are used as training data.

18. The system of claim 13, wherein the final trained set of neural networks are used in an analysis mode to automatically recognize and analyze the echocardiogram images in the patient studies of the respective labs.

19. The system of claim 18, wherein the software component automatically recognizes and analyzes echocardiogram images by:
receiving, from a memory, one of the patient studies comprising a plurality of echocardiogram images;
separating the plurality of echocardiogram (echo) images according to 2D images and Doppler modality images;
classifying the 2D images by view type;
extracting features of the Doppler modality images and using the extracted features to classify the Doppler modality images by region;
segmenting each classified 2D view type to produce segmented 2D images;
segmenting each classified the Doppler modality region to generate waveform traces to produce segmented Doppler modality images;
using both the segmented 2D images and the segmented Doppler modality images to calculate for the patient study measurements of cardiac features for both left and right sides of the heart;
generating conclusions by comparing the calculated measurements with International cardiac guidelines; and
outputting a report highlighting ones of the calculated measurements that fall outside of the International cardiac guidelines.

20. The system of claim 19, wherein the final trained set of neural networks are implemented in the analysis mode as:
a first neural network to classify the 2D images by view type;
a second set of neural networks to both extract features from Doppler modality images and to use the extracted features to classify the Doppler modality images by region;
a third set of neural networks for each classified 2D view type in order to segment the cardiac chambers in the 2D images and produce segmented 2D images; and
a fourth set of neural networks for each classified Doppler modality region in order to segment Doppler modality images to generate waveform traces.

21. The system of claim 20, wherein the final trained set of neural networks includes a set of one or more prediction CNNs for disease prediction and a set of one or more prognosis CNNs for disease prognosis.

22. The system of claim 20, wherein the first neural network and the second set of neural networks comprise convolutional neural networks (CNNs).

23. The system of claim 19, wherein the third set of neural networks comprise generative adversarial neural networks (GANs).

24. The system of claim 20, wherein another set of the GANs is used at least in part to generate artificial segmentation training data and classification training data.

25. An executable software product stored on a non-transitory computer-readable medium containing program instructions for training neural networks of an automated workflow, the program instructions for:
downloading and installing a client and a set of neural networks to a first remote computer of a first laboratory, the lightweight client accessing the echocardiogram image files of the first laboratory to train the set of neural networks and to upload a first trained set of neural networks to the server;
downloading and installing the client and the first trained set of neural networks to a second remote computer of a second laboratory, the lightweight client accessing the echocardiogram image files of the second laboratory to continue to train the first trained set of neural networks and to upload a second trained set of neural networks to the server; and
continuing the process until the client and the second trained set of neural networks is downloaded and installed to a last remote computer of a last laboratory, the lightweight client accessing the echocardiogram image files of the last laboratory to continue to train the second trained set of neural networks and to upload a final trained set of neural networks to the server.

* * * * *